(12) United States Patent
Andreas et al.

(10) Patent No.: US 8,080,048 B2
(45) Date of Patent: Dec. 20, 2011

(54) STENT DELIVERY FOR BIFURCATED VESSELS

(75) Inventors: Bernard Andreas, Redwood City, CA (US); Jeffry J. Grainger, Portola Valley, CA (US)

(73) Assignee: Xtent, Inc., Menlo Park, CA (US)

( * ) Notice: Subject to any disclaimer, the term of this patent is extended or adjusted under 35 U.S.C. 154(b) by 1040 days.

(21) Appl. No.: 10/814,593

(22) Filed: Mar. 30, 2004

(65) Prior Publication Data

US 2004/0249434 A1 Dec. 9, 2004

Related U.S. Application Data

(63) Continuation-in-part of application No. 10/637,713, filed on Aug. 8, 2003, now Pat. No. 7,309,350, which is a continuation-in-part of application No. 10/412,714, filed on Apr. 10, 2003, now Pat. No. 7,137,993, and a continuation-in-part of application No. 10/306,813, filed on Nov. 27, 2002, now abandoned.

(60) Provisional application No. 60/364,389, filed on Mar. 13, 2002, provisional application No. 60/336,767, filed on Dec. 3, 2001.

(51) Int. Cl.
*A61F 2/82* (2006.01)
(52) U.S. Cl. ...................................... 623/1.11; 623/1.35
(58) Field of Classification Search ........ 623/1.11–1.54, 623/903; 606/108, 194
See application file for complete search history.

(56) References Cited

U.S. PATENT DOCUMENTS

| | | | |
|---|---|---|---|
| 4,069,825 A | 1/1978 | Akiyama | |
| 4,468,224 A | 8/1984 | Enzmann et al. | |
| 4,512,338 A | 4/1985 | Balko | |
| 4,564,014 A | 1/1986 | Fogarty et al. | |
| 4,580,568 A | 4/1986 | Gianturco | |
| 4,681,110 A | 7/1987 | Wiktor | |
| 4,690,684 A | 9/1987 | McGreevy et al. | |
| 4,733,665 A | 3/1988 | Palmaz | |

(Continued)

FOREIGN PATENT DOCUMENTS

DE 1 963 0469 1/1998

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner* — Elizabeth Houston
(74) *Attorney, Agent, or Firm* — Kilpatrick Townsend and Stockton LLP; Kenneth Shurtz

(57) ABSTRACT

Apparatus and methods for delivering stents to bifurcated vessels involve delivering a first stent in a main branch of a vessel using a stent delivery catheter and delivering a second stent in a side branch of the vessel, without removing the stent delivery catheter from the patient. In various embodiments, multiple stents may be placed in either or both of the main and side branches. In some embodiments, stents in main and side branches are separate and do not touch, while in other embodiments a side branch stent may extend through a sidewall opening in a main branch stent. Stent length may optionally be adjusted in situ, and some embodiments provide for predilatation of one or more lesions.

27 Claims, 17 Drawing Sheets

U.S. PATENT DOCUMENTS

| | | | |
|---|---|---|---|
| 4,739,762 A | 4/1988 | Palmaz | |
| 4,762,129 A | 8/1988 | Bonzel | |
| 4,770,176 A | 9/1988 | McGreevy et al. | |
| 4,775,337 A | 10/1988 | Van Wagener et al. | |
| 4,776,337 A | 10/1988 | Palmaz | |
| 4,886,062 A | 12/1989 | Wiktor | |
| 4,891,225 A | 1/1990 | Langer et al. | |
| 4,988,356 A | 1/1991 | Crittenden et al. | |
| 4,994,066 A | 2/1991 | Voss | |
| 4,994,069 A | 2/1991 | Ritchart et al. | |
| 5,013,318 A | 5/1991 | Spranza, III | |
| 5,035,706 A | 7/1991 | Giantureo et al. | |
| 5,040,548 A | 8/1991 | Yock | |
| 5,064,435 A | 11/1991 | Porter | |
| 5,092,877 A | 3/1992 | Pinchuk | |
| 5,102,417 A | 4/1992 | Palmaz | |
| 5,104,404 A | 4/1992 | Wolff | |
| 5,122,154 A | 6/1992 | Rhodes | |
| 5,135,535 A | 8/1992 | Kramer | |
| 5,195,984 A | 3/1993 | Schatz | |
| 5,217,495 A | 6/1993 | Kaplan et al. | |
| 5,219,355 A | 6/1993 | Parodi et al. | |
| 5,226,913 A | 7/1993 | Pinchuk | |
| 5,246,421 A | 9/1993 | Saab | |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,334,187 A | 8/1994 | Fischell et al. | |
| 5,421,955 A | 6/1995 | Lau et al. | |
| 5,445,646 A * | 8/1995 | Euteneuer et al. | 606/198 |
| 5,456,713 A | 10/1995 | Chuter | |
| 5,458,615 A | 10/1995 | Klemm et al. | |
| 5,478,349 A | 12/1995 | Nicholas | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,593,412 A | 1/1997 | Martinez et al. | |
| 5,607,444 A | 3/1997 | Lam | |
| 5,607,463 A | 3/1997 | Schwartz et al. | |
| 5,628,775 A | 5/1997 | Jackson et al. | |
| 5,634,928 A * | 6/1997 | Fischell et al. | 623/1.11 |
| 5,639,274 A | 6/1997 | Fischell et al. | |
| 5,662,675 A | 9/1997 | Polanskyj Stockert et al. | |
| 5,670,161 A | 9/1997 | Healy et al. | |
| 5,676,654 A | 10/1997 | Ellis et al. | |
| 5,683,451 A | 11/1997 | Lenker et al. | |
| 5,697,948 A | 12/1997 | Marin et al. | |
| 5,697,971 A * | 12/1997 | Fischell et al. | 623/1.15 |
| 5,702,418 A | 12/1997 | Ravenscroft | |
| 5,709,701 A | 1/1998 | Parodi | |
| 5,716,393 A | 2/1998 | Lindenberg et al. | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,741,323 A | 4/1998 | Pathak et al. | |
| 5,749,848 A | 5/1998 | Jang et al. | |
| 5,749,921 A | 5/1998 | Lenker et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,797,951 A | 8/1998 | Mueller et al. | |
| 5,800,519 A | 9/1998 | Sandock | |
| 5,807,398 A * | 9/1998 | Shaknovich | 623/1.11 |
| 5,824,040 A | 10/1998 | Cox et al. | |
| 5,824,041 A | 10/1998 | Lenker et al. | |
| 5,833,694 A * | 11/1998 | Poncet | 623/1.11 |
| 5,836,964 A | 11/1998 | Richter et al. | |
| 5,843,092 A | 12/1998 | Heller et al. | |
| 5,855,563 A | 1/1999 | Kaplan et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,899,935 A | 5/1999 | Ding | |
| 5,902,332 A | 5/1999 | Schatz | |
| 5,919,175 A | 7/1999 | Sirhan | |
| 5,922,020 A | 7/1999 | Klein et al. | |
| 5,961,536 A | 10/1999 | Mickley et al. | |
| 5,968,069 A | 10/1999 | Dusbabek et al. | |
| 5,972,027 A | 10/1999 | Johnson | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,997,563 A | 12/1999 | Kretzers et al. | |
| 6,004,328 A | 12/1999 | Solar | |
| 6,007,517 A | 12/1999 | Anderson | |
| 6,022,359 A | 2/2000 | Frantzen | |
| 6,022,374 A | 2/2000 | Imran | |
| 6,033,434 A * | 3/2000 | Borghi | 623/1.35 |
| 6,036,725 A | 3/2000 | Avellanet | |
| 6,039,721 A | 3/2000 | Johnson et al. | |
| 6,042,589 A | 3/2000 | Marianne | |
| 6,056,722 A | 5/2000 | Jayaraman | |
| 6,066,155 A | 5/2000 | Amann et al. | |
| 6,068,655 A | 5/2000 | Seguin et al. | |
| 6,070,589 A | 6/2000 | Keith et al. | |
| 6,090,063 A | 7/2000 | Makower et al. | |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler | |
| 6,132,460 A | 10/2000 | Thompson | |
| 6,143,016 A | 11/2000 | Bleam et al. | |
| 6,165,167 A | 12/2000 | Delaloye | |
| 6,165,210 A | 12/2000 | Lau et al. | |
| 6,179,878 B1 | 1/2001 | Duering et al. | |
| 6,183,509 B1 * | 2/2001 | Dibie | 623/1.35 |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,238,991 B1 | 5/2001 | Suzuki | |
| 6,241,691 B1 | 6/2001 | Ferrera et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,264,688 B1 | 7/2001 | Herklotz et al. | |
| 6,267,783 B1 | 7/2001 | Letendre et al. | |
| 6,273,895 B1 | 8/2001 | Pinchuk et al. | |
| 6,273,911 B1 | 8/2001 | Cox et al. | |
| 6,273,913 B1 | 8/2001 | Wright et al. | |
| 6,312,458 B1 | 11/2001 | Golds | |
| 6,315,794 B1 | 11/2001 | Richter | |
| 6,319,277 B1 | 11/2001 | Rudnick et al. | |
| 6,322,586 B1 | 11/2001 | Monroe et al. | |
| 6,325,823 B1 | 12/2001 | Horzewski et al. | |
| 6,334,871 B1 | 1/2002 | Dor et al. | |
| 6,344,272 B1 | 2/2002 | Oldenburg et al. | |
| 6,357,104 B1 | 3/2002 | Myers | |
| 6,375,676 B1 | 4/2002 | Cox | |

| Patent | Date | Inventor | Ref |
|---|---|---|---|
| 6,379,365 B1 | 4/2002 | Diaz | |
| 6,383,171 B1 | 5/2002 | Gifford et al. | |
| 6,409,753 B1 | 6/2002 | Brown et al. | |
| 6,415,696 B1 | 7/2002 | Erickeson et al. | |
| 6,419,693 B1 | 7/2002 | Fariabi | |
| 6,425,898 B1 | 7/2002 | Wilson et al. | |
| 6,428,811 B1 | 8/2002 | West et al. | |
| 6,451,025 B1 | 9/2002 | Jervis | |
| 6,451,050 B1 | 9/2002 | Rudakov et al. | |
| 6,464,720 B2 | 10/2002 | Boatman et al. | |
| 6,468,298 B1 | 10/2002 | Pelton | |
| 6,468,299 B2 | 10/2002 | Stack et al. | |
| 6,485,510 B1 | 11/2002 | Camrud et al. | |
| 6,488,694 B1 | 12/2002 | Lau et al. | |
| 6,488,702 B1 | 12/2002 | Besselink | |
| 6,511,468 B1 | 1/2003 | Cragg et al. | |
| 6,520,986 B2 | 2/2003 | Martin et al. | |
| 6,520,987 B1 * | 2/2003 | Plante | 623/1.16 |
| 6,527,789 B1 | 3/2003 | Lau et al. | |
| 6,527,799 B2 | 3/2003 | Shanley | |
| 6,529,549 B1 | 3/2003 | Norrell et al. | |
| 6,530,944 B2 | 3/2003 | West et al. | |
| 6,540,777 B2 | 4/2003 | Stenzel | |
| 6,551,350 B1 | 4/2003 | Thornton et al. | |
| 6,555,157 B1 | 4/2003 | Hossainy | |
| 6,569,180 B1 | 5/2003 | Sirhan et al. | |
| 6,575,993 B1 | 6/2003 | Yock | |
| 6,579,305 B1 | 6/2003 | Lashinski | |
| 6,579,309 B1 * | 6/2003 | Loos et al. | 623/1.16 |
| 6,582,394 B1 | 6/2003 | Reiss et al. | |
| 6,582,460 B1 | 6/2003 | Cryer | |
| 6,585,756 B1 | 7/2003 | Strecker | |
| 6,592,549 B2 | 7/2003 | Gerdts et al. | |
| 6,599,296 B1 | 7/2003 | Gillick et al. | |
| 6,599,314 B2 | 7/2003 | Mathis | |
| 6,602,282 B1 | 8/2003 | Yan | |
| 6,605,062 B1 | 8/2003 | Hurley et al. | |
| 6,605,109 B2 | 8/2003 | Fiedler | |
| 6,607,553 B1 | 8/2003 | Healy et al. | |
| 6,645,517 B2 | 11/2003 | West | |
| 6,645,547 B1 | 11/2003 | Shekalim et al. | |
| 6,656,212 B2 | 12/2003 | Ravenscroft et al. | |
| 6,660,031 B2 | 12/2003 | Tran et al. | |
| 6,660,381 B2 | 12/2003 | Halas et al. | |
| 6,666,883 B1 | 12/2003 | Seguin et al. | |
| 6,676,695 B2 | 1/2004 | Solem | |
| 6,679,909 B2 | 1/2004 | McIntosh et al. | |
| 6,685,730 B2 | 2/2004 | West et al. | |
| 6,692,465 B2 | 2/2004 | Kramer | |
| 6,699,280 B2 | 3/2004 | Camrud et al. | |
| 6,699,724 B1 | 3/2004 | West et al. | |
| 6,702,843 B1 | 3/2004 | Brown | |
| 6,709,379 B1 | 3/2004 | Brandau et al. | |
| 6,709,440 B2 * | 3/2004 | Callol et al. | 606/108 |
| 6,712,827 B2 | 3/2004 | Ellis et al. | |
| 6,712,845 B2 | 3/2004 | Hossainy | |
| 6,723,071 B2 | 4/2004 | Gerdts et al. | |
| 6,736,842 B2 | 5/2004 | Healy et al. | |
| 6,743,251 B1 | 6/2004 | Eder | |
| 6,761,734 B2 * | 7/2004 | Suhr | 623/1.35 |
| 6,778,316 B2 | 8/2004 | Halas et al. | |
| 6,800,065 B2 | 10/2004 | Clarke et al. | |
| 6,835,203 B1 * | 12/2004 | Vardi et al. | 623/1.34 |
| 6,837,901 B2 | 1/2005 | Rabkin et al. | |
| 6,849,084 B2 | 2/2005 | Rabkin et al. | |
| 6,852,252 B2 | 2/2005 | Halas et al. | |
| 6,855,125 B2 * | 2/2005 | Shanley | 604/102.02 |
| 6,858,034 B1 | 2/2005 | Hijlkema et al. | |
| 6,878,161 B2 | 4/2005 | Lenker | |
| 6,893,417 B2 | 5/2005 | Gribbons et al. | |
| 6,896,695 B2 | 5/2005 | Mueller et al. | |
| 6,918,928 B2 | 7/2005 | Wolinsky et al. | |
| 6,939,376 B2 | 9/2005 | Shulz et al. | |
| 6,945,989 B1 | 9/2005 | Betelia et al. | |
| 6,951,053 B2 | 10/2005 | Padilla et al. | |
| 7,005,454 B2 | 2/2006 | Brocchini et al. | |
| 7,037,327 B2 | 5/2006 | Salmon et al. | |
| 7,090,694 B1 * | 8/2006 | Morris et al. | 623/1.15 |
| 7,101,840 B2 | 9/2006 | Brocchini et al. | |
| 7,137,993 B2 * | 11/2006 | Acosta et al. | 623/1.11 |
| 7,147,655 B2 * | 12/2006 | Chermoni | 623/1.11 |
| 7,182,779 B2 | 2/2007 | Acosta et al. | |
| 7,192,440 B2 | 3/2007 | Andreas et al. | |
| 7,241,308 B2 | 7/2007 | Andreas et al. | |
| 7,270,668 B2 | 9/2007 | Andreas et al. | |
| 7,294,146 B2 | 11/2007 | Chew et al. | |
| 7,300,456 B2 | 11/2007 | Andreas et al. | |
| 7,309,350 B2 * | 12/2007 | Landreville et al. | 623/1.11 |
| 7,314,480 B2 * | 1/2008 | Eidenschink et al. | 623/1.11 |
| 7,320,702 B2 | 1/2008 | Hammersmark et al. | |
| 7,323,006 B2 | 1/2008 | Andreas et al. | |
| 7,326,236 B2 | 2/2008 | Andreas et al. | |
| 2001/0020154 A1 | 9/2001 | Bigus et al. | |
| 2001/0020181 A1 | 9/2001 | Layne | |
| 2001/0044595 A1 | 11/2001 | Reydel et al. | |
| 2001/0044632 A1 | 11/2001 | Daniel et al. | |
| 2001/0049547 A1 | 12/2001 | Moore | |
| 2002/0037358 A1 | 3/2002 | Barry et al. | |
| 2002/0091439 A1 | 7/2002 | Baker et al. | |
| 2002/0107560 A1 * | 8/2002 | Richter | 623/1.11 |
| 2002/0111671 A1 | 8/2002 | Stenzel | |
| 2002/0128706 A1 | 9/2002 | Ospyka | |
| 2002/0138132 A1 | 9/2002 | Brown | |
| 2002/0151924 A1 | 10/2002 | Shiber | |
| 2002/0151955 A1 | 10/2002 | Tran et al. | |
| 2002/0156496 A1 * | 10/2002 | Chermoni | 606/194 |
| 2002/0177890 A1 | 11/2002 | Lenker | |
| 2002/0183763 A1 * | 12/2002 | Callol et al. | 606/108 |
| 2002/0183343 A1 | 12/2002 | Mathis | |
| 2002/0188347 A1 | 12/2002 | Mathis | |
| 2002/0193873 A1 * | 12/2002 | Brucker et al. | 623/1.35 |
| 2003/0045923 A1 | 3/2003 | Bashiri et al. | |
| 2003/0093143 A1 | 5/2003 | Zhao et al. | |
| 2003/0097169 A1 | 5/2003 | Brucker el al. | |
| 2003/0114912 A1 | 6/2003 | Sequin et al. | |
| 2003/0114919 A1 | 6/2003 | McQuiston et al. | |
| 2003/0114922 A1 | 6/2003 | Iwasaka et al. | |
| 2003/0125791 A1 | 7/2003 | Sequin et al. | |
| 2003/0125800 A1 | 7/2003 | Shulze et al. | |
| 2003/0125802 A1 * | 7/2003 | Callol et al. | 623/1.35 |
| 2003/0135259 A1 * | 7/2003 | Simso | 623/1.12 |
| 2003/0135266 A1 | 7/2003 | Chew et al. | |
| 2003/0139796 A1 | 7/2003 | Sequin et al. | |
| 2003/0139797 A1 | 7/2003 | Johnson et al. | |
| 2003/0139798 A1 | 7/2003 | Brown et al. | |
| 2003/0163085 A1 | 8/2003 | Tanner et al. | |
| 2003/0176909 A1 | 9/2003 | Kusleika | |
| 2003/0191516 A1 | 10/2003 | Weldon et al. | |
| 2003/0195609 A1 | 10/2003 | Berenstein | |
| 2003/0199821 A1 | 10/2003 | Gerdts et al. | |
| 2003/0204238 A1 | 10/2003 | Tedeschi | |
| 2003/0212447 A1 | 11/2003 | Euteneuer | |
| 2003/0225446 A1 | 12/2003 | Hartley | |
| 2004/0024450 A1 | 2/2004 | Shulze et al. | |
| 2004/0030380 A1 | 2/2004 | Shulze et al. | |
| 2004/0044395 A1 | 3/2004 | Nelson | |
| 2004/0087965 A1 | 5/2004 | Levine et al. | |
| 2004/0093061 A1 | 5/2004 | Acosta et al. | |
| 2004/0093067 A1 | 5/2004 | Israel | |
| 2004/0093077 A1 | 5/2004 | White et al. | |
| 2004/0098081 A1 | 5/2004 | Landreville et al. | |
| 2004/0111145 A1 | 6/2004 | Serino et al. | |
| 2004/0117008 A1 | 6/2004 | Wnendt et al. | |
| 2004/0176832 A1 | 9/2004 | Hartley et al. | |
| 2004/0186551 A1 | 9/2004 | Kao et al. | |
| 2004/0193245 A1 | 9/2004 | Deem et al. | |
| 2004/0215165 A1 | 10/2004 | Coyle et al. | |
| 2004/0215312 A1 | 10/2004 | Andreas | |
| 2004/0243217 A1 | 12/2004 | Andersen et al. | |
| 2004/0249435 A1 | 12/2004 | Andreas et al. | |
| 2005/0010276 A1 | 1/2005 | Acosta et al. | |
| 2005/0038505 A1 | 2/2005 | Shulze et al. | |
| 2005/0049673 A1 | 3/2005 | Andreas et al. | |
| 2005/0080474 A1 | 4/2005 | Andreas et al. | |
| 2005/0080475 A1 | 4/2005 | Andreas et al. | |
| 2005/0090846 A1 | 4/2005 | Pedersen et al. | |
| 2005/0101624 A1 | 5/2005 | Betts et al. | |
| 2005/0125051 A1 | 6/2005 | Eidenschink et al. | |

| | | | | | |
|---|---|---|---|---|---|
| 2005/0131008 A1 | 6/2005 | Betts et al. | WO | WO 9837833 A1 * | 9/1998 |
| 2005/0133164 A1 | 6/2005 | Fischer et al. | WO | WO 98/58600 | 12/1998 |
| 2005/0143827 A1 | 6/2005 | Globerman et al. | WO | WO 99/01087 | 1/1999 |
| 2005/0149159 A1 | 7/2005 | Andreas et al. | WO | WO 00/12832 A3 | 3/2000 |
| 2005/0165378 A1 | 7/2005 | Heinrich et al. | WO | WO 00/15151 | 3/2000 |
| 2005/0209674 A1 | 9/2005 | Kutscher et al. | WO | WO 00/25841 | 5/2000 |
| 2005/0222671 A1 | 10/2005 | Schaeffer et al. | WO | WO 00/32136 | 6/2000 |
| 2005/0228477 A1 | 10/2005 | Grainger et al. | WO | WO 00/41649 | 7/2000 |
| 2005/0245637 A1 | 11/2005 | Hossainy et al. | WO | WO 00/50116 | 8/2000 |
| 2005/0288763 A1 | 12/2005 | Andreas et al. | WO | WO 00/62708 | 10/2000 |
| 2005/0288764 A1 | 12/2005 | Snow et al. | WO | WO 00/72780 | 12/2000 |
| 2005/0288766 A1 | 12/2005 | Plain et al. | WO | WO 01/70297 | 9/2001 |
| 2006/0069424 A1 | 3/2006 | Acosta et al. | WO | WO 01/91918 | 12/2001 |
| 2006/0200223 A1 | 9/2006 | Andreas et al. | WO | WO 02/085253 | 10/2002 |
| 2006/0206190 A1 | 9/2006 | Chermoni | WO | WO 03/022178 | 3/2003 |
| 2006/0229700 A1 | 10/2006 | Acosta et al. | WO | WO 03/047651 | 6/2003 |
| 2006/0229706 A1 | 10/2006 | Shulze et al. | WO | WO 03/051425 | 6/2003 |
| 2006/0271150 A1 | 11/2006 | Andreas et al. | WO | WO 03/075797 | 9/2003 |
| 2006/0271151 A1 | 11/2006 | McGarry et al. | WO | WO 2004/017865 | 3/2004 |
| 2006/0282147 A1 | 12/2006 | Andreas et al. | WO | WO 2004/043299 | 5/2004 |
| 2006/0282149 A1 | 12/2006 | Kao | WO | WO 2004/043301 | 5/2004 |
| 2006/0282150 A1 | 12/2006 | Olson et al. | WO | WO 2004/043510 | 5/2004 |
| 2006/0287726 A1 | 12/2006 | Segal et al. | WO | WO 2004/052237 A2 | 6/2004 |
| 2007/0027521 A1 | 2/2007 | Andreas et al. | WO | WO 2005/013853 | 2/2005 |
| 2007/0067012 A1 | 3/2007 | George et al. | WO | WO 2006/036939 | 4/2006 |
| 2007/0088368 A1 | 4/2007 | Acosta et al. | WO | WO 2006/047520 | 5/2006 |
| 2007/0088420 A1 | 4/2007 | Andreas et al. | WO | WO 2007/035805 | 3/2007 |
| 2007/0088422 A1 | 4/2007 | Chew et al. | WO | WO 2007/053187 | 5/2007 |
| 2007/0100423 A1 | 5/2007 | Acosta et al. | WO | WO 2007/146411 | 12/2007 |
| 2007/0100424 A1 | 5/2007 | Chew et al. | WO | WO 2008/005111 | 1/2008 |
| 2007/0106365 A1 | 5/2007 | Andreas et al. | | | |
| 2007/0118202 A1 | 5/2007 | Chermoni | | | |
| 2007/0118203 A1 | 5/2007 | Chermoni | | | |
| 2007/0118204 A1 | 5/2007 | Chermoni | | | |
| 2007/0129733 A1 | 6/2007 | Will et al. | | | |
| 2007/0156225 A1 | 7/2007 | George et al. | | | |
| 2007/0156226 A1 | 7/2007 | Chew et al. | | | |
| 2007/0179587 A1 | 8/2007 | Acosta et al. | | | |
| 2007/0219612 A1 | 9/2007 | Andreas et al. | | | |
| 2007/0219613 A1 | 9/2007 | Kao et al. | | | |
| 2007/0265637 A1 | 11/2007 | Andreas et al. | | | |
| 2007/0270936 A1 | 11/2007 | Andreas et al. | | | |
| 2007/0276461 A1 | 11/2007 | Andreas et al. | | | |
| 2007/0281117 A1 | 12/2007 | Kaplan et al. | | | |
| 2007/0292518 A1 | 12/2007 | Ludwig | | | |
| 2008/0071345 A1 | 3/2008 | Hammersmark et al. | | | |
| 2008/0077229 A1 | 3/2008 | Andreas et al. | | | |
| 2008/0097299 A1 | 4/2008 | Andreas et al. | | | |
| 2008/0097574 A1 | 4/2008 | Andreas et al. | | | |
| 2008/0147162 A1 | 6/2008 | Andreas et al. | | | |
| 2008/0199510 A1 | 8/2008 | Ruane et al. | | | |
| 2008/0234795 A1 | 9/2008 | Snow et al. | | | |
| 2008/0269865 A1 | 10/2008 | Snow et al. | | | |

FOREIGN PATENT DOCUMENTS

| | | |
|---|---|---|
| EP | 0 203 945 B2 | 12/1986 |
| EP | 0 274 129 B1 | 7/1988 |
| EP | 0 282 143 | 9/1988 |
| EP | 0 505 686 | 9/1992 |
| EP | 0 533 960 | 3/1993 |
| EP | 714640 A1 * | 6/1996 |
| EP | 0 596 145 | 5/1997 |
| EP | 0 947 180 | 10/1999 |
| EP | 1 258 230 | 11/2002 |
| EP | 1 277 449 | 1/2003 |
| EP | 1 318 765 | 6/2003 |
| EP | 1523959 A2 | 4/2005 |
| EP | 1523960 A2 | 4/2005 |
| EP | 1266638 B1 | 10/2005 |
| JP | 03-133446 | 6/1991 |
| JP | 10-503663 | 4/1998 |
| JP | 10-295823 | 11/1998 |
| JP | 2001-190687 | 7/2001 |
| WO | WO 95/29647 | 11/1995 |
| WO | WO 96/26689 | 9/1996 |
| WO | WO 96/33677 | 10/1996 |
| WO | WO 97/46174 | 12/1997 |
| WO | WO 97/48351 | 12/1997 |
| WO | WO 98/20810 | 5/1998 |

OTHER PUBLICATIONS

Thierry et al. "Approach to Coronary Bifurcation Stenting in 2003," Euro PCR, (May 2003) 28 pages total.

Cooley et al., "Applications of Ink-Jet Printing Technology to BioMEMs and Microfluidic Systems," Proceedings, SPIE Conference on Microfluidics and BioMEMs, (Oct. 2001).

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

"STENT". Definitions from Dictionary.com Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 61/012,317, filed Dec. 7, 2007, first named inventor: Patrick Ruane.

U.S. Appl. No. 09/097,855, filed Jun. 15, 1998, first named inventor: Enrique J. Klein.

U.S. Appl. No. 09/225,364, filed Jan. 4, 1999, first named inventor: Aaron V. Kaplan.

U.S. Appl. No. 10/874,859, filed Jun. 22, 2004, first named inventor: Pablo Acosta.

U.S. Appl. No. 11/462,951, filed Aug. 7, 2006, first named inventor: David Snow.
U.S. Appl. No. 11/627,096, filed Jan. 25, 2007, first named inventor: Bernard Andreas.
U.S. Appl. No. 11/689,927, filed Mar. 22, 2007, first named inventor: David Snow.
U.S. Appl. No. 11/752,448, filed May 23 2007, first named inventor: David Snow.
U.S. Appl. No. 11/771,929, filed Jun. 29, 2007, first named inventor: David Snow.
U.S. Appl. No. 11/857,562, filed Sep. 19, 2007, first named inventor: Bryan Mao.
U.S. Appl. No. 11/938,730, filed Nov. 12, 2007, first named inventor: Sunmi Chew.
U.S. Appl. No. 11/945,142, filed Nov. 26, 2007, first named inventor: Bernard Andreas.
U.S. Appl. No. 11/947,677, filed Nov. 29, 2007, first named inventor: Dan Hammersmark.
U.S. Appl. No. 11/952,644, filed Dec. 7, 2007, first named inventor: Bernard Andreas.
U.S. Appl. No. 11/953,242, filed Dec. 10, 2007, first named inventor: Bernard Andreas.
U.S. Appl. No. 12/033,586, filed Feb. 19, 2008, first named inventor: Patrick H. Ruane.
U.S. Appl. No. 12/040,598, filed Feb. 29, 2008, first named inventor: Bernard Andreas.
Supplementary European Search Report of EP Patent Application No. 05727731.1, dated Mar. 25, 2008, 2 pages total.
Supplementary European Search Report of EP Patent Application No. 05744136, dated Mar. 26, 2008, 3 pages total.
U.S. Appl. No. 12/040,598, filed Feb. 29, 2008, first named inventor: Bernard Andreas.
U.S. Appl. No. 12/043,513, filed Mar. 6, 2008, first named inventor: David Lowe.
U.S. Appl. No. 12/061,951, filed Apr. 3, 2008, first named inventor: Stephen Kao.
U.S. Appl. No. 12/109,477, filed Apr. 25, 2008, first named inventor: Stephen Kao.
U.S. Appl. No. 12/127,147, filed May 27, 2008, first named inventor: Sunmi Chew.
U.S. Appl. No. 12/133,909, filed Jun. 5, 2008, first named inventor: David Sanderson.
"Drug Delivery Stent With Holes Located on Neutral Axis" Research Disclosure, Kenneth Mason Publications, Hampshire, CB, No. 429, Jan. 2000, p. 13, XP00976354.

* cited by examiner

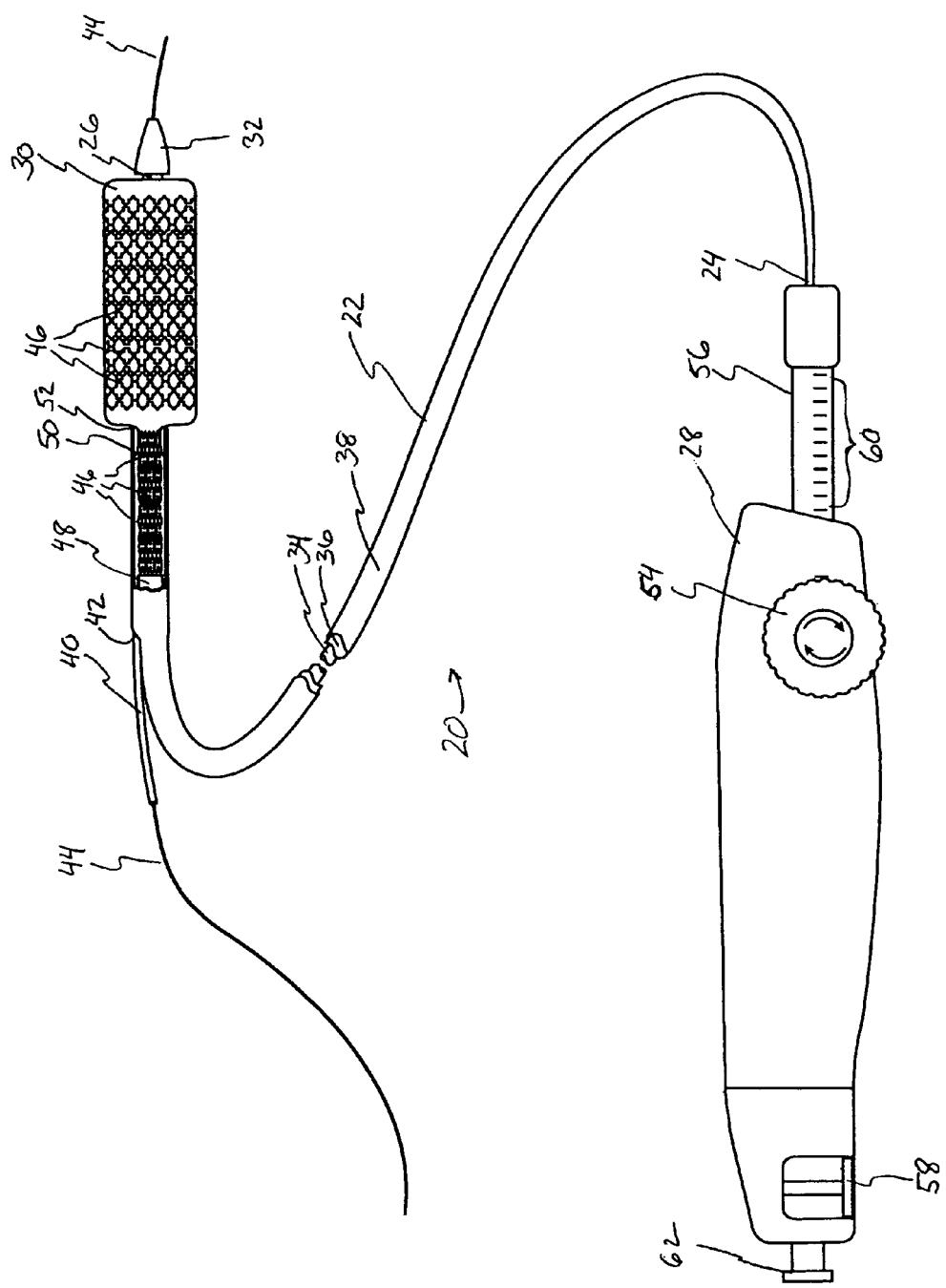

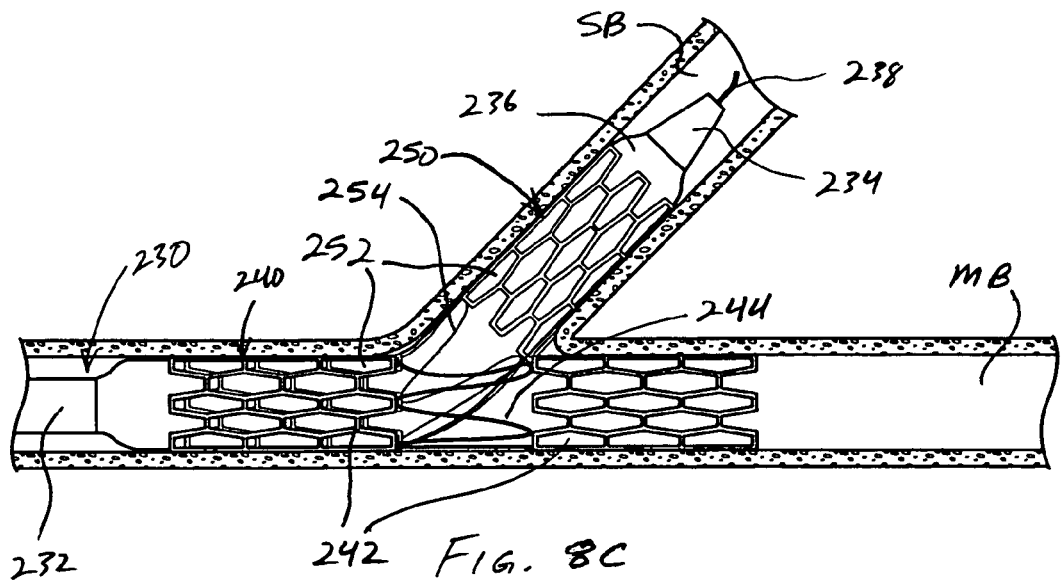
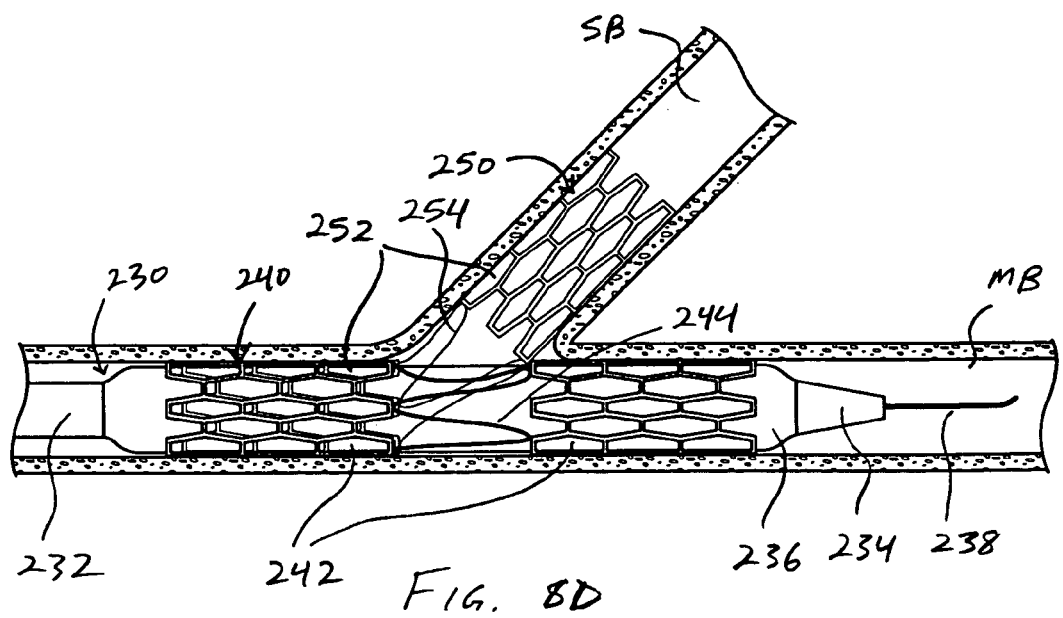

STENT DELIVERY FOR BIFURCATED VESSELS

CROSS REFERENCE TO RELATED APPLICATIONS

This application is a continuation-in-part of U.S. patent application Ser. No. 10/637,713, filed Aug. 8, 2003, which is a continuation-in-part of co-pending application Ser. No. 10/412,714, filed Apr. 10, 2003, which is a continuation-in-part of application Ser. No. 10/306,813, filed Nov. 27, 2002, which is a non-provisional application of U.S. Provisional Application Ser. Nos. 60/336,767, filed Dec. 3, 2001, and 60/364,389, filed Mar. 13, 2002, the disclosures of which are all fully incorporated herein by reference. This application is related to U.S. patent application Ser. No. 10/738,666, filed Dec. 16, 2003, and U.S. Provisional Patent Application No. 60/440,839, filed Jan. 17, 2003, the disclosures of which are all fully incorporated herein by reference.

FIELD OF THE INVENTION

This invention relates generally to stents and stent delivery catheters for deployment in the coronary arteries and other vessels. More specifically, the invention relates to stents and stent delivery systems for treating bifurcated vessels.

BACKGROUND OF THE INVENTION

Stenting has become an increasingly important treatment option for patients with coronary artery disease. Stenting involves the placement of a tubular prosthesis within a diseased coronary artery to expand the arterial lumen and maintain the patency of the artery. Early stent technology suffered from problems with restenosis, the tendency of the coronary artery to become re-occluded following stent placement. However, in recent years, improvements in stent design and the advent of drug-eluting stents have reduced restenosis rates dramatically. As a result, the number of stenting procedures being performed in the United States, Europe, and elsewhere has soared.

Stents are delivered to the coronary arteries using long, flexible vascular catheters typically inserted through a femoral artery. For self-expanding stents, the stent is simply released from the delivery catheter and it resiliently expands into engagement with the vessel wall. For balloon expandable stents, a balloon on the delivery catheter is expanded which expands and deforms the stent to the desired diameter, whereupon the balloon is deflated and removed.

Current stent delivery technology suffers from a number of drawbacks. For example, current stent delivery catheters are not capable of customizing the length of the stent in situ to match the size of the lesion to be treated. While lesion size may be measured prior to stenting using angiography or fluoroscopy, such measurements may be inexact. If a stent is introduced that is found to be of inappropriate size, the delivery catheter and stent must be removed from the patient and replaced with a different device of correct size.

Moreover, current stent delivery devices cannot treat multiple lesions with a single catheter. Current devices are capable of delivering only a single stent with a single catheter, and if multiple lesions are to be treated, a new catheter and stent must be introduced for each lesion to be treated.

Further, current stent delivery devices are not well-adapted for treating vascular lesions that are very long and/or in curved regions of a vessel. Current stents have a discrete length that is relatively short due to their stiffness. If current stents were made longer so as to treat longer lesions, they would not conform well to the curvature of vessels or to the movement of vessels on the surface of the beating heart. On the other hand, any attempt to place multiple stents end-to-end in longer lesions is hampered by the inability to maintain appropriate inter-stent spacing and to prevent overlap of adjacent stents.

Many of the above shortcomings are addressed by various currently pending patent applications assigned to the assignee of the present application, such as U.S. patent application Ser. Nos. 10/306,622, filed Nov. 27, 2002; 10/306,620, filed Nov. 27, 2002; 10/306,813, filed Nov. 27, 2002; 10/412,714, filed Apr. 10, 2003; 10/637,713, filed Aug. 8, 2003; 10/624,451, filed Jul. 21, 2003; 10/738,666, filed Dec. 16, 2003; 10/458,062, filed Jun. 9, 2003; 10/686,507, filed Oct. 14, 2003; 10/686,025, filed Oct. 14, 2003; 10/687,532, filed Oct. 15, 2003; 10/46466, filed Dec. 23, 2003; and 10/794,405, filed Mar. 3, 2004, all of which are hereby incorporated fully by reference. Although many improvements in stent design and stent delivery techniques have been suggested, improvements are still being sought.

For example, repair of vessels at areas of bifurcation is particularly challenging. A bifurcation of a vessel is generally a division into two branches, such as a main branch and a side branch. Generally, treatment of such bifurcated vessels with stents is difficult because it is technically challenging to place one or more stents in a main vessel and one or more stents in a branching vessel so as to sufficiently treat the existing lesion(s) while not interrupting blood flow through either the main or branch vessel. Oftentimes, if the main vessel is treated sufficiently with a stent, the stent disrupts flow into the branching vessel and/or makes placement of additional stents in the branching vessel quite difficult. In other cases, placement of a stent in the branching vessel may hinder stent placement and/or blood flow in the main vessel. Difficulties in stent-based treatment of bifurcated vessels occur due to limitations of both current stent designs and currently available stent delivery devices and techniques.

Some currently available systems for placing stents at an area of vessel bifurcation require placement of a first stent in one branch of the vessel, removal of the catheter from the body, insertion of a second catheter to place a second stent, and so on until a desired number of stents is placed. Other available techniques involve insertion of two catheters simultaneously to place stents in two branches of a bifurcated vessel. A number of other alternative techniques and devices have been developed for treating vessel lesions at bifurcations. Some methods are described, for example, in U.S. Pat. Nos. 6,033,434 and 6,582,394, as well as PCT Patent Application Publication No. WO 2004/017865.

All of these currently available devices and methods for delivering stents at vessel bifurcations have one or more drawbacks. Perhaps most obvious is the inconvenience and additional time and expense of using multiple catheters to place multiple stents in the bifurcated vessel. As discussed above, currently available devices and methods also do not provide for placement of custom length stents.

For these and other reasons, stents and stent delivery catheters are needed which facilitate treatment of vessels at areas of bifurcations. Ideally, such stents and delivery catheters would allow for placement of stents in a main vessel and a branch vessel, without requiring removal of the delivery catheter from the patient. Also ideally, customization of stent length in situ would be provided, as well as treatment of multiple lesions of various sizes, both without requiring removal of the delivery catheter from the patient. Such stents and stent delivery catheters should be capable of treating lesions of particularly long length and lesions in curved regions of a vessel, and should be highly flexible to conform to vessel shape and movement. Such stent delivery catheters should further be of minimal cross-sectional profile and should be highly flexible for endovascular positioning through tortuous vascular pathways. At least some of these objectives will be met by the present invention.

BRIEF SUMMARY OF THE INVENTION

The invention provides apparatus and methods for delivering prostheses or stents into bifurcated vessels. In one aspect of the invention, a method of treating one or more lesions in a vessel, the vessel having a main branch and a side branch branching from the main branch at a bifurcation, involves: positioning a delivery catheter in the main branch; deploying a first stent from the delivery catheter in the main branch; positioning the delivery catheter in the side branch; and deploying a second stent from the delivery catheter in the side branch. Using this method, the delivery catheter is not removed from the vessel between deploying the first and second stents.

In some embodiments, the method may optionally include deploying a third stent from the delivery catheter in the main branch or side branch without removing the delivery catheter from the vessel. In one embodiment, the delivery catheter is positioned through an opening in a sidewall of the first stent to deploy the second stent. In a preferred embodiment, the first and second stents each comprise a plurality of separable segments. Optionally, the first stent may have a different length than the second stent. In alternative embodiments, the first stent may be deployed before the second stent or the second stent may be deployed before the first stent. In some embodiments, the first stent and the second stent each have a portion in the main branch. Some embodiments of the method further include adjusting the length of the first and/or second stents before deploying the first and/or second stents while the delivery catheter remains in the vessel.

Optionally, some embodiments further include dilating at least one lesion in the vessel using an expandable member on the delivery catheter before deploying at least one of the first and second stents. Such dilating of a vessel before deploying a stent is often referred to as "pre-dilatation." In various embodiments, various different techniques for pre-dilatation and stent placement may be employed. For example, in one embodiment an expandable member may be used to pre-dilate a vessel, and then the same expandable member may be used to deploy an expandable stent. Sometimes, the same expandable member may additionally be used to further expand the stent after it has been deployed. In another embodiment, an expandable member may be used to pre-dilate a vessel and then self-expanding stent(s) may be deployed from the delivery catheter without using the expandable member for deployment. In another embodiment, a first expandable member may be used for pre-dilatation and a second expandable member on the same delivery catheter may be used to deploy stent(s) in the vessel. Thus, any suitable combination of expandable members, pre-dilatation and stent delivery are contemplated within the scope of the invention. Stent delivery devices and methods involving pre-dilatation are described more fully in U.S. patent application Ser. No. 10/794,405, entitled "Stent Delivery Apparatus and Methods," filed Mar. 3, 2004, which was previously incorporated by reference.

In another aspect of the invention, a method of treating one or more lesions in a vessel, the vessel having a first branch and a second branch meeting at a bifurcation, involves: positioning a delivery catheter in the first branch; deploying a first stent from the delivery catheter in the first branch, a portion of the first stent being disposed across the bifurcation; positioning the delivery catheter in the second branch through an opening in a sidewall of the first stent; and deploying a second stent from the delivery catheter, at least a portion of the second stent being disposed in the second branch. Again, using this method, the delivery catheter is not removed from the vessel between deploying the first and second stents.

In some embodiments, the method further includes dilating the opening in the sidewall of the first stent by expanding an expandable member on the delivery catheter. In one embodiment, before dilating, the opening in the sidewall of the first stent is I-shaped. Optionally, the first stent may have a first portion with a plurality of first slots and a second portion with a plurality of second slots, the first slots being larger than the second slots. In such embodiments, the opening in the sidewall of the first stent may comprise one of the first slots, and the first stent may be deployed so that at least one of the first slots is aligned with bifurcation.

In various embodiments, any of a number of suitable stents may be used. In one embodiment, for example, the first stent may have a different geometry than the second stent. In another embodiment, the first stent has a different length than the second stent. In some embodiments, at least one of the first and second stents comprises a plurality of separable segments.

As described above, in some embodiments deploying the first stent and/or the second stent comprises expanding an expandable member on the delivery catheter. In other embodiments, the stents may be self-expanding and may be deployed by releasing them from the delivery catheter. Some embodiments may further include dilating at least one lesion in the vessel using an expandable member on the delivery catheter before deploying at least one of the first and second stents.

In another aspect of the invention, a stent delivery device for treating one or more lesions in a vessel having a bifurcation, the bifurcation including a main branch and a side branch, includes: a catheter shaft; a first stent carried by the catheter shaft configured for deployment in the main branch; a second stent carried by the catheter shaft configured for deployment in the side branch; and a deployment mechanism for deploying the first and second stents independently of each other. In some embodiments, the deployment mechanism comprises an expandable member coupled to the catheter shaft, the first and second stents being positionable on the expandable member for expansion thereby. Such embodiments may optionally further include a sheath slidably disposed over the expandable member, the sheath being positionable to restrain a first portion of the expandable member while allowing expansion of a second portion of the expandable member. In some embodiments, the expandable member is configured for dilation of the vessel without deploying either of the first and second stents.

In some embodiments, either or both of the first and second stents may be self-expanding. Optionally, at least one of the first and second stents may have a sidewall opening that can be widened following stent deployment. In such embodiments, the other of the first and second stents may optionally be positionable through the sidewall opening. In one embodiment, the second stent has a different geometry, material, shape, and/or size than the first stent. Some embodiments further include a third stent carried by the catheter shaft and deployable independently of the first and second stents. In some embodiments, a length of at least one of the first and second stents may be selected in situ. Also in some embodiments, at least one of the first and second stents may comprise a plurality of separable stent segments.

Further aspects of the nature and advantages of the invention will become apparent from the detailed description below taken in conjunction with the drawings.

BRIEF DESCRIPTION OF THE DRAWINGS

FIG. 1 is a perspective view of a stent delivery catheter with sheath retracted and expandable member inflated according to one embodiment of the invention.

FIGS. 8A-8D are side cutaway views illustrating a method for treating lesions in a bifurcated vessel using a stent delivery catheter according to another embodiment of the invention.

DETAILED DESCRIPTION OF THE INVENTION

Figure 2A:
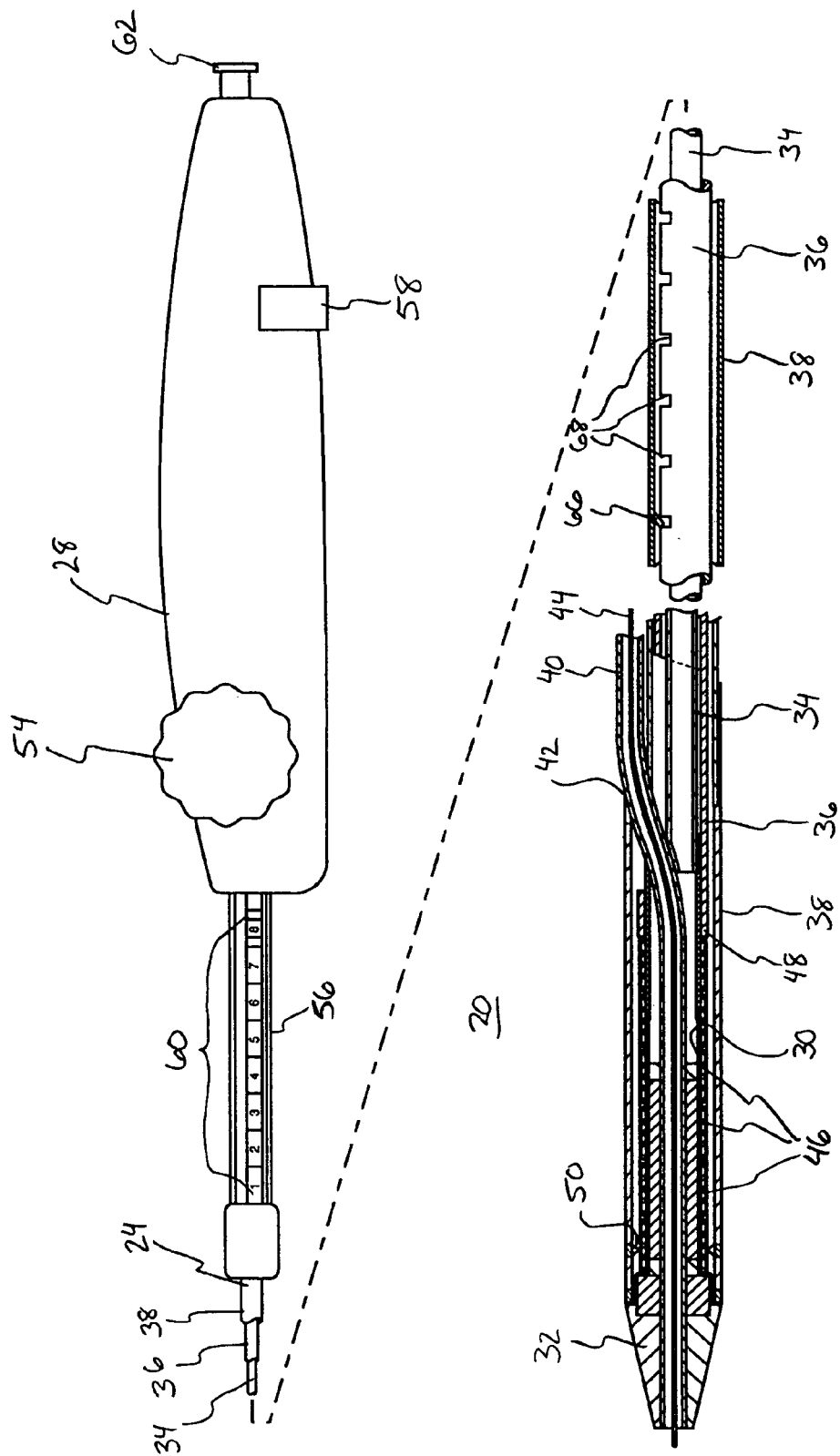
FIG. 2A is a side cross-section of a distal portion of the stent delivery catheter of FIG. 1 with expandable member deflated and sheath advanced distally.

Referring to FIG. 1, in a first embodiment of the invention, a stent delivery catheter 20 comprises an elongate flexible shaft 22 having a proximal end 24 and a distal end 26. Shaft 22 is comprised of a plurality of coaxial members including an inflation shaft 34, a pusher 36, and a sheath 38. A handle 28 is mounted to sheath 38 at proximal end 24. Near distal end 26, expandable member 30, shown in an expanded configuration, is mounted at its proximal end to inflation shaft 34. A guidewire tube 40 extends through a port 42 in sheath 38 and extends through the interior of expandable member 30 to distal end 26. Expandable member 30 is attached at its distal end to guidewire tube 40, and a nosecone 32 is mounted to guidewire tube 40 distally of expandable member 30. A guidewire 44 is slidably positionable through guidewire tube 40 and nosecone 32 to facilitate guidance of catheter 20 through the vasculature.

A plurality of stent segments 46 are slidably positioned over expandable member 30. Pusher 36 is axially slidable relative to inflation shaft 34 and engages stent segments 46 at its distal end 48. Pusher 36 may be pushed distally to advance stent segments 46 over expandable member 30, or pusher 36 may be held in a stationary position while expandable member 30 is drawn proximally relative to stent segments 46. Sheath 38 is axially movable relative to expandable member 30, pusher 36, and stent segments 46. Sheath 38 may be repositioned proximally or distally to selectively expose a desired length of the expandable member and stent segments thereon according to the length of the lesion to be treated. Sheath 38 and pusher 36 may be drawn proximally in tandem relative to expandable member 30 to separate stent segments 46 exposed distally of sheath 38 from stent segments 46 held within sheath 38. Various other aspects of the construction of delivery catheter 20 and stent segments 46 are described in copending U.S. patent application Ser. No. 10/637,713, which was previously incorporated by reference.

A stent valve 50 is mounted to the interior of sheath 38 and is preferably spaced proximally from the distal end 52 of sheath 38 a distance equal to the length of about ½-1 stent segment. Stent valve 50 comprises an annular ridge configured to frictionally engage stent segments 46 to facilitate control of the spacing between those segments to be deployed distally of sheath 38 and those to be retained within sheath 38. Stent valve 50 may also comprise any of the structures described in copending U.S. patent application Ser. No. 10/412,714, which was previously incorporated by reference.

Handle 28 includes an actuator knob 54 rotatably coupled thereto. A post 56 is mounted to handle 28 so as to be extendable distally out of the handle and retractable proximally into the handle. Sheath 39 is attached to post 56. Rotation of actuator knob 54 extends or retracts post 56, thereby moving sheath 38 relative to expandable member 30. A lever 58 is pivotably coupled to handle 28 and is movable between a first position in which rotation of actuator knob 54 moves only sheath 38, and a second position in which rotation of actuator knob 54 moves both sheath 38 and pusher 36 relative to expandable member 30, as described more fully below.

A plurality of indicia 60 are disposed on post 56. Indicia 60 comprise alphanumeric symbols or other appropriate indicators of the length of expandable member exposed distally of sheath 38 and/or the number or length of stent segments 46 exposed for deployment. As described more fully below, a pointer or other reference object may be used that points to the appropriate location among indicia 60 corresponding to the number or length of stent segments 46 that have been exposed; preferably such pointer is adapted to compensate for retraction of sheath 38 in tandem with pusher 36, during which additional stent segments are not exposed distally of sheath 38, as described more fully below.

A luer fitting 62 is mounted to a proximal end of handle 28 and is in fluid communication with an inflation lumen (not shown in FIG. 1) in inflation shaft 34. Luer fitting 62 is adapted for coupling to an inflation device to enable delivery of inflation fluid into expandable member 30, for example, an Indeflator™ inflation device available from Guidant Corp. of Santa Clara, Calif.

Figure 2B:
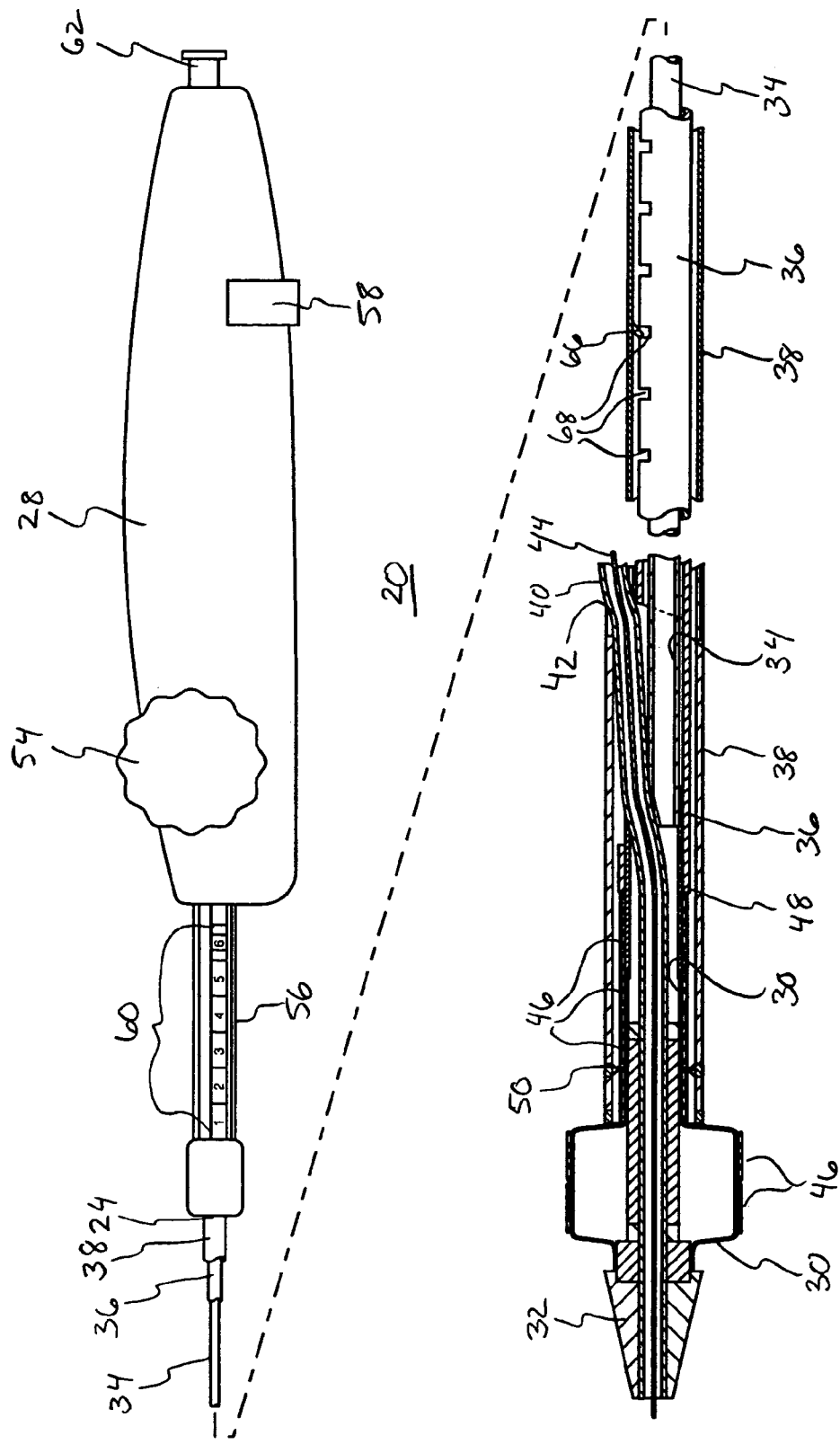
FIG. 2B is a side cross-section of a distal portion of the stent delivery catheter of FIG. 1 with expandable member inflated and sheath retracted.

Referring to FIGS. 2A-2B, delivery catheter 20 includes a device for providing a tactile indication of the number of stent segments 46 exposed from sheath 38 in addition to the visual indication provided by indicia 60. In this embodiment, the indication device consists of a detent 66 extending inwardly from the inner wall of sheath 38, and a series of slots 68 arranged axially at spaced-apart locations on pusher 36. Detent 66 and slots 68 may be located in a distal portion of delivery catheter 20 just proximal to expandable member 30, in a middle portion of the catheter proximal to guidewire port 42, or near the proximal end 24 distally of or within post 56 or handle 28. Detent 66 is preferably a cantilevered extension integrally formed with sheath 38, being cut, for example, out of the wall of sheath 38, and is resiliently deflectable and biased toward pusher 36. Detent 66 may alternatively be a bump or ridge on the inner wall of sheath 38 configured to engage slots 68. Slots 68 may be holes, apertures, depressions, recesses, ridges, bumps or any other suitable structure for receiving or catching on detent 66. The spacing of slots 68 is selected to provide an indication of the distance that sheath 38 is translated relative to pusher 36. In a preferred embodiment, the spacing is equal to the length of 1 stent segment 46, although ½, twice, or other known fraction or multiple of the length of a stent segment 46 are also possible. As sheath 38 is retracted proximally relative to pusher 36, detent 66 catches in each slot, providing a tactile "bump" that can be felt through handle 28. In this way, as knob 54 is turned to retract sheath 38, the user knows that each bump corresponds to the length of one stent segment, meaning that one stent segment has been exposed distally of sheath 38 with each bump. By feeling such bumps and by observing indicia 60, the user can precisely retract the sheath to expose the number of stent segments needed to match the length of the lesion being treated, as illustrated in FIG. 2B.

Further description of stent delivery catheter devices such as those illustrated by FIGS. 1, 2A and 2B may be found in U.S. patent application Ser. No. 10/46466, which was previously incorporated by reference. Further detailed description of the distal portion of a stent delivery catheter may be found in U.S. patent application Ser. No. 10/794,405, which was previously incorporated by reference.

Figure 3A:
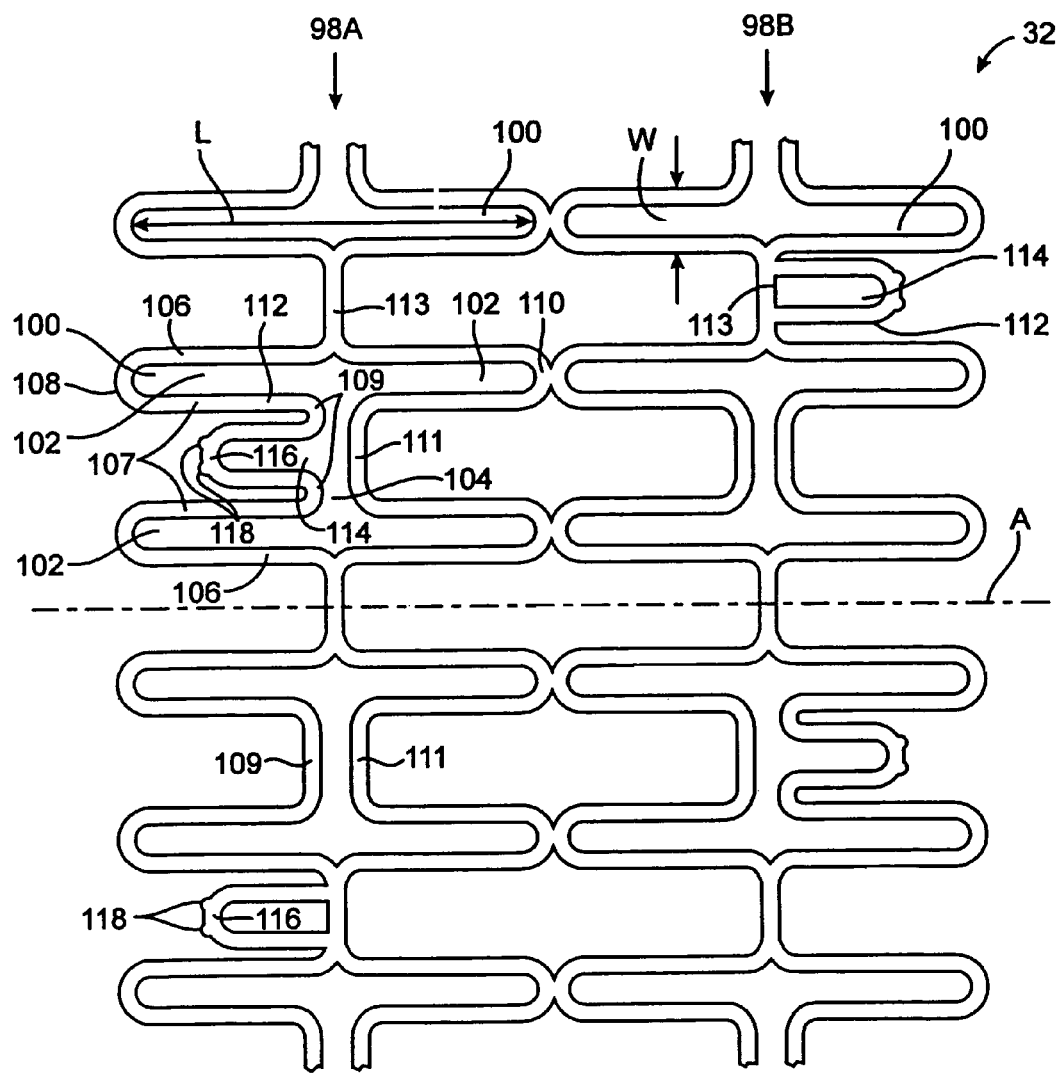
FIG. 3A is a side view of a first embodiment of a stent segment in an unexpanded configuration according to one embodiment of the invention.
Figure 3B:
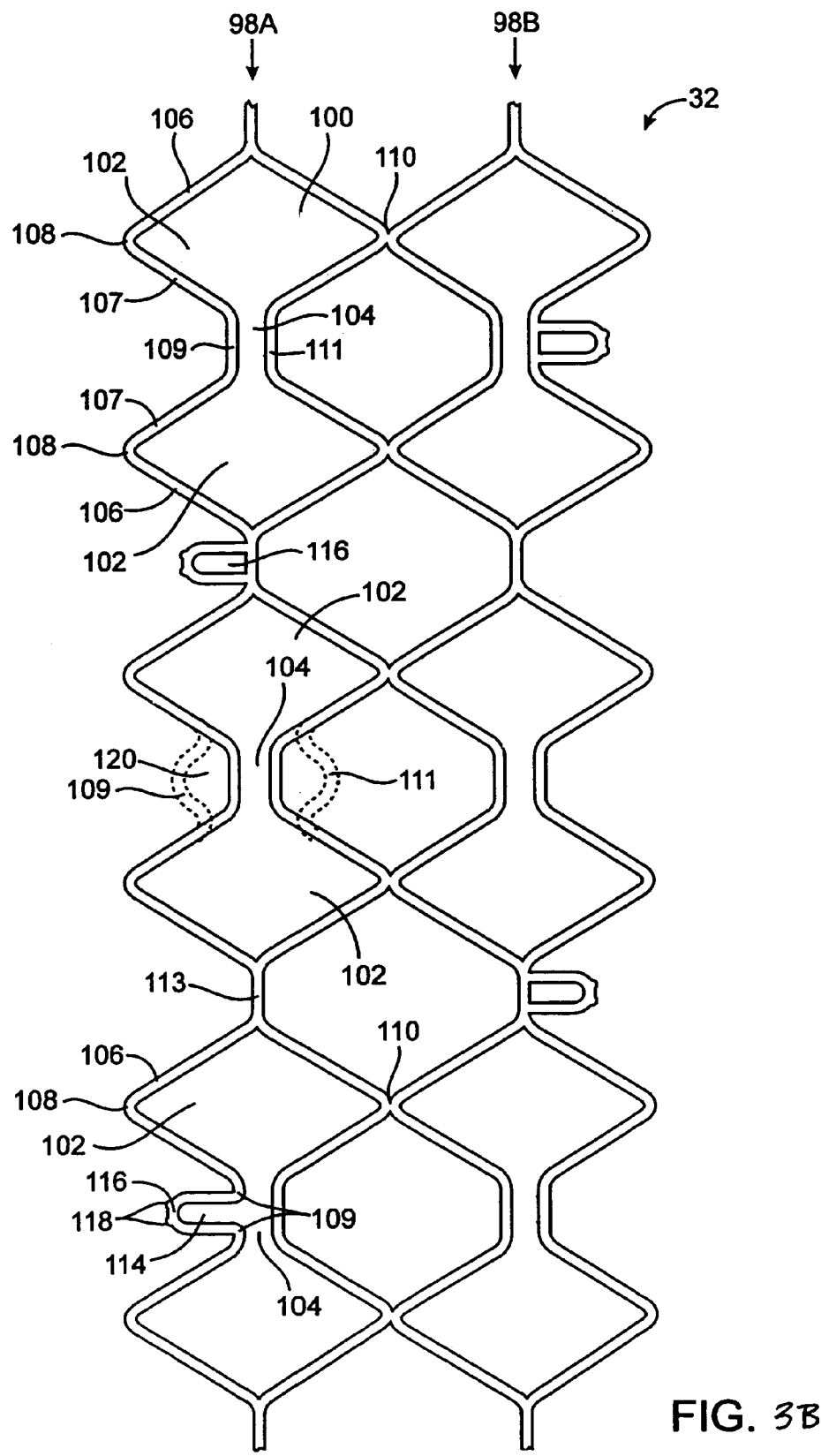
FIG. 3B is a side view of the stent segment of FIG. 3A in an expanded configuration.

A first preferred geometry of stent segments 32 is illustrated in FIGS. 3A-3B. FIG. 3A illustrates a portion of a stent segment 32 in an unexpanded configuration, shown in a planar shape for clarity. Stent segment 32 comprises two parallel rows 96A, 96B of I-shaped cells 100 formed around an axis A so that stent segment 32 has a cylindrical shape. Each cell 100 has upper and lower axial slots 102 aligned with the axial direction and a circumferential slot 104. Upper and lower slots 102 preferably have an oval, racetrack, rectangular or other oblong shape with a long dimension L generally parallel to axis A and a short dimension W perpendicular thereto. Axial slots 102 are bounded by upper axial struts 106 and lower axial struts 107, curved outer ends 108 and curved inner ends 110. Each circumferential slot 104 is bounded by an outer circumferential strut 109 and an inner circumferential strut 111. Each I-shaped cell 100 is connected to the adjacent I-shaped cell 100 in the same row 96A or 96B by a circumferential connecting strut 113. All or a portion of cells 100 in row 96A merge or join with cells 100 in row 96B at the inner ends 110, which are integrally formed with the inner ends 110 of the adjacent cells 100.

In a preferred embodiment, a spacing member 112 extends outwardly in the axial direction from a selected number of outer circumferential struts 109 and/or connecting struts 113. Spacing member 112 preferably itself forms a subcell 114 in its interior, but alternatively may be solid without any cell or opening therein. For those spacing members 112 attached to outer circumferential struts 109, subcell 114 preferably communicates with I-shaped cell 100. Spacing members 112 are configured to engage the curved outer ends 108 of an adjacent stent segment 32 so as to maintain appropriate spacing between adjacent stent segments. In one embodiment, spacing members 112 have outer ends 116 with two spaced-apart protrusions 118 that provide a cradle-like structure to index and stabilize the curved outer end 108 of the adjacent stent segment. Preferably, spacing members 112 have an axial length of at least about 10%, more preferably at least about 25%, of the long dimension L of I-shaped cells 100, so that the I-shaped cells 100 of adjacent stent segments are spaced apart at least that distance. Because spacing members 112 experience little or no axial shortening during expansion of stent segments 32, this minimum spacing between stent segments is maintained both in the unexpanded and expanded configurations.

FIG. 3B shows stent segment 32 of FIG. 3A in an expanded configuration. It may be seen that cells 100 are expanded so that upper and lower slots 102 are diamond shaped with circumferential slots 104 remaining basically unchanged. This results in some axial shortening of the stent segment, thereby increasing the spacing between adjacent stent segments. The stent geometry is optimized by balancing the amount of axial shortening and associated inter-segment spacing, the desired degree of vessel wall coverage, the desired metal density, and other factors. Because the stent is comprised of multiple unconnected stent segments 32, any desired number from 2 up to 10 or more stent segments may be deployed simultaneously to treat lesions of any length. Further, because such segments are unconnected to each other, the deployed stent structure is highly flexible and capable of deployment in long lesions having curves and other complex shapes.

As an additional feature, circumferential slots 104 provide a pathway through which vessel side branches can be accessed for catheter interventions. Should stent segment 32 be deployed at a location in which it covers the ostium of a side branch to which access is desired, a balloon dilatation catheter may be positioned through circumferential slot 104 and expanded. This deforms circumferential struts 109, 111 axially outward, thereby expanding circumferential slot 104 and further expanding upper and lower slots 102, as shown in phantom in FIG. 3B. This provides a relatively large opening 120 through which a catheter may be inserted through stent segment 32 and into the side branch for placing stents, performing angioplasty, or carrying out other interventions. In preferred embodiments, opening 120 may be expanded to a diameter approximately as large as the expanded diameter of stent segments 32 to allow deployment of additional stent segments through opening 120.

Figure 4A:
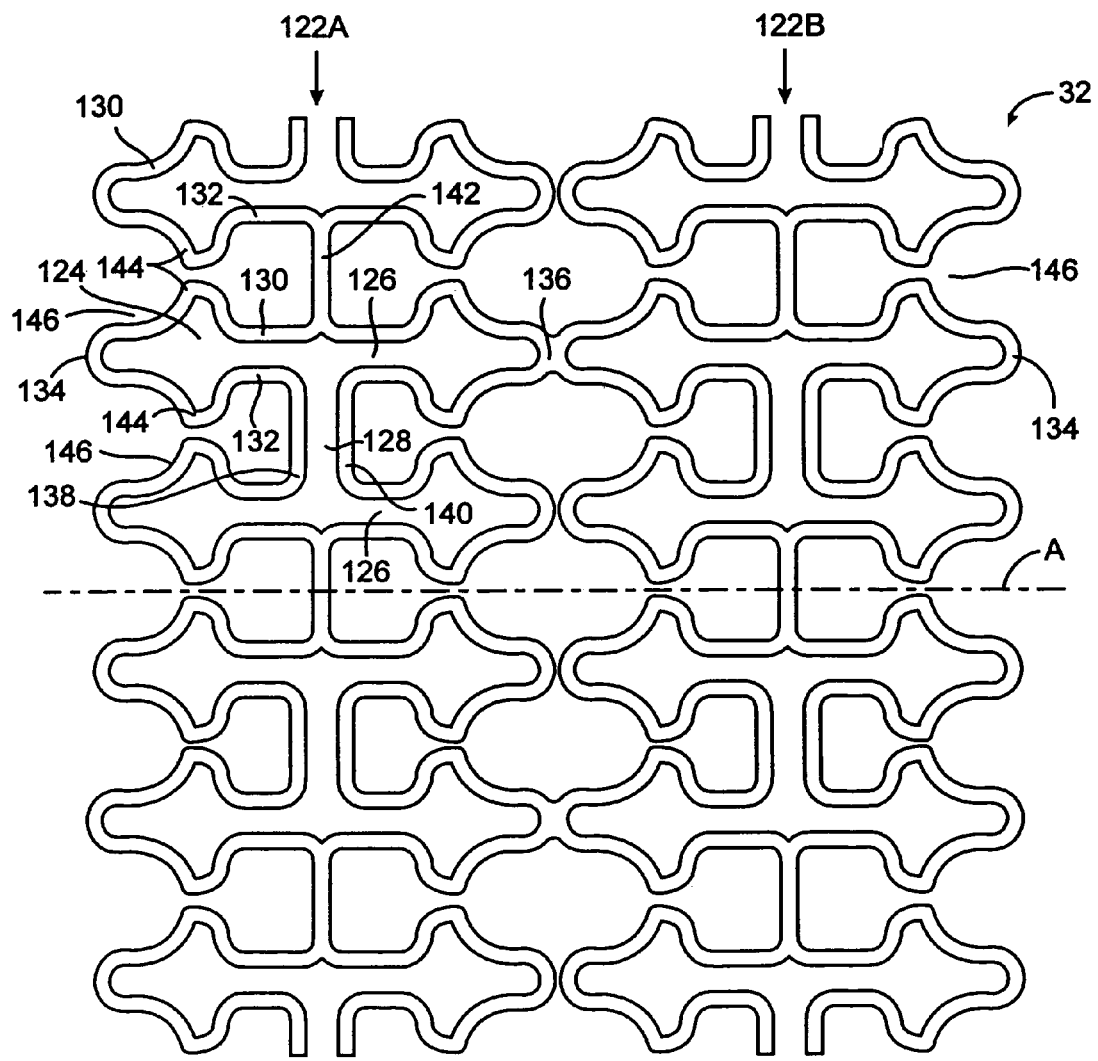
FIG. 4A is a side view of a stent segment in an unexpanded configuration according to one embodiment of the invention.
Figure 4B:
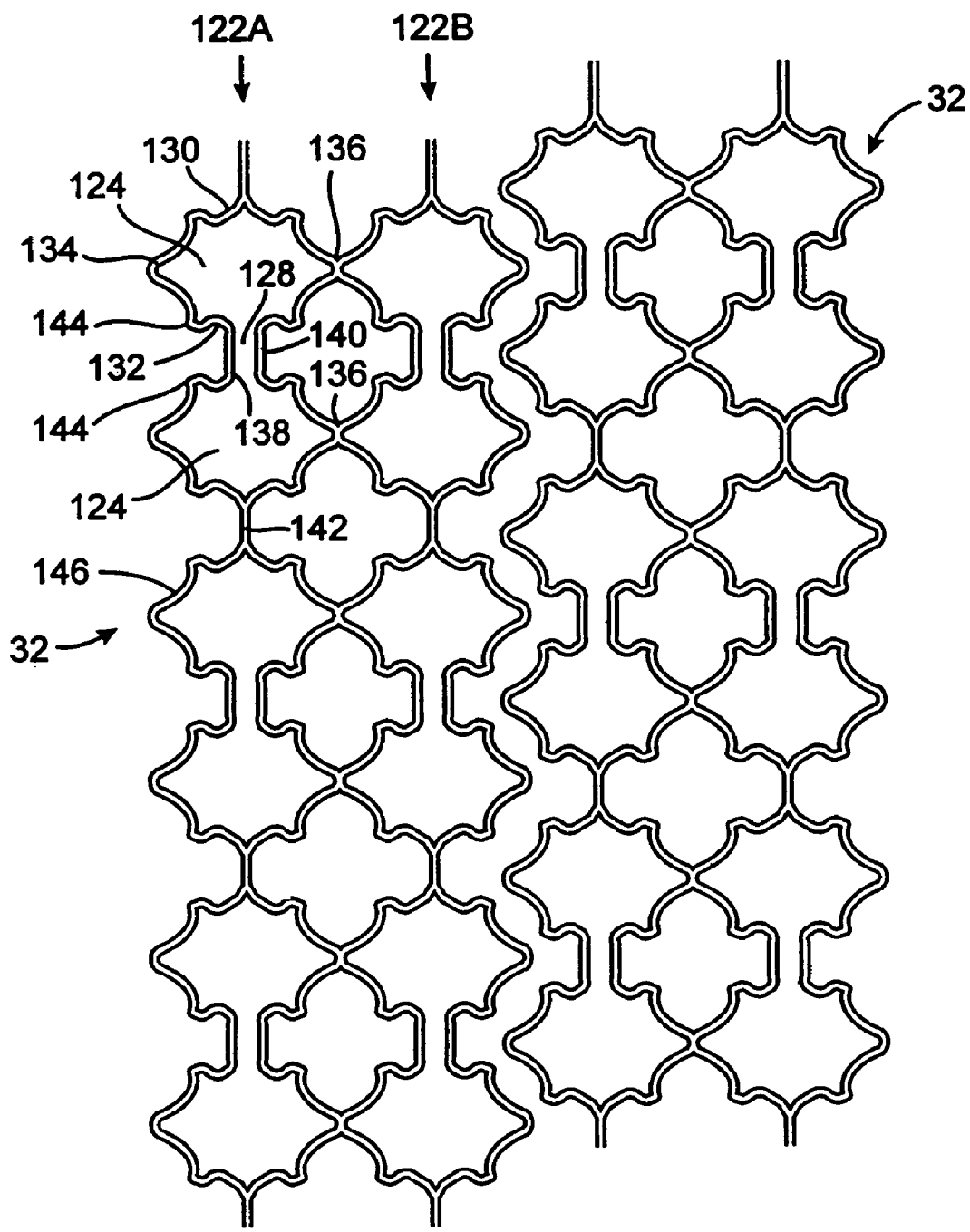
FIG. 4B is a side view of two of the stent segments of FIG. 4A in an expanded configuration.

FIGS. 4A-4B illustrate a second preferred embodiment of a stent segment 32 according to the invention. In FIG. 4A, a portion of stent segment 32 is shown in a planar shape for clarity. Similar to the embodiment of FIG. 3A, stent segment 32 comprises two parallel rows 122A, 122B of I-shaped cells 124 formed into a cylindrical shape around axial axis A. Cells 124 have upper and lower axial slots 126 and a connecting circumferential slot 128. Upper and lower slots 126 are bounded by upper axial struts 130, lower axial struts 132, curved outer ends 134, and curved inner ends 136. Circumferential slots 128 are bounded by outer circumferential strut 138 and inner circumferential strut 140. Each I-shaped cell 124 is connected to the adjacent I-shaped cell 124 in the same row 122 by a circumferential connecting strut 142. Row 122A is connected to row 122B by the merger or joining of curved inner ends 136 of at least one of upper and lower slots 126 in each cell 124.

One of the differences between the embodiment of FIGS. 4A-4B and that of FIGS. 3A-3B is the way in which spacing is maintained between adjacent stent segments. In place of the spacing members 112 of the earlier embodiment, the embodiment of FIG. 4A includes a bulge 144 in upper and lower axial struts 130, 132 extending circumferentially outwardly from axial slots 126. These give axial slots 126 an arrowhead or cross shape at their inner and outer ends. The bulge 144 in each upper axial strut 130 extends toward the bulge 144 in a lower axial strut 132 in the same cell 100 or in an adjacent cell 100, thus creating a concave abutment 146 in the space between each axial slot 126. Concave abutments 146 are configured to receive and engage curved outer ends 134 of cells 124 in the adjacent stent segment, thereby maintaining spacing between the stent segments. The axial location of bulges 144 along upper and lower axial struts 130, 132 may be selected to provide the desired degree of inter-segment spacing.

FIG. 4B shows two stent segments 32 of FIG. 4A in an expanded condition. It may be seen that axial slots 124 are deformed into a circumferentially widened modified diamond shape with bulges 144 on the now diagonal upper and lower axial struts 130, 132. Circumferential slots 128 are generally the same size and shape as in the unexpanded configuration. Bulges 144 have been pulled away from each other to some extent, but still provide a concave abutment 146 to maintain a minimum degree of spacing between adjacent stent segments. As in the earlier embodiment, some axial shortening of each segment occurs upon expansion and stent geometry can be optimized to provide the ideal intersegment spacing.

It should also be noted that the embodiment of FIGS. 4A-4B retains the feature described above with respect to FIGS. 3A-3B to enable access to vessel side branches blocked by stent segment 32. Should such side branch access be desired, a dilatation catheter may be inserted into circumferential slot 128 and expanded to provide an enlarged opening through which a side branch may be entered.

Referring now to FIGS. 5A-5D, various embodiments of stents 30 may include a side access portion 152 and adjacent end portions 150. In some embodiments, side access portions 152 are configured with larger openings than end portions 150 to allow passage of a guidewire, stent delivery catheter and/or stent through the sidewall of side access portion 152. In other embodiments, side access portion 152 has struts which are made of a more flexible or deformable material to facilitate passage of a second stent therethrough. Thus, stent 30 may be placed in a main branch vessel with side access portion 152 positioned at an ostium of a side branch vessel bifurcating off of the main branch. A stent delivery catheter may then be passed through an opening in side access portion 152, into the side branch vessel, to place a second stent in the side branch. In some embodiments, the side branch stent may extend though side access portion 152 into the main branch. Methods for deploying such stents are described in further detail below.

Figure 5A:
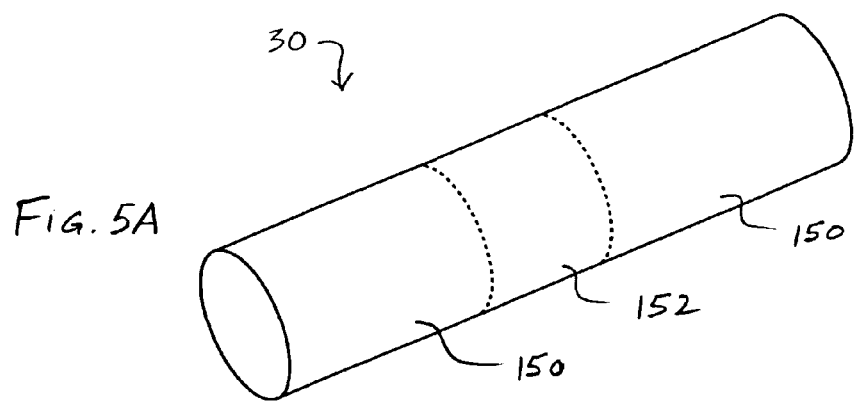
FIG. 5A is a perspective schematic view of a stent having a central portion and adjacent end portions according to one embodiment of the invention.
Figure 5B:
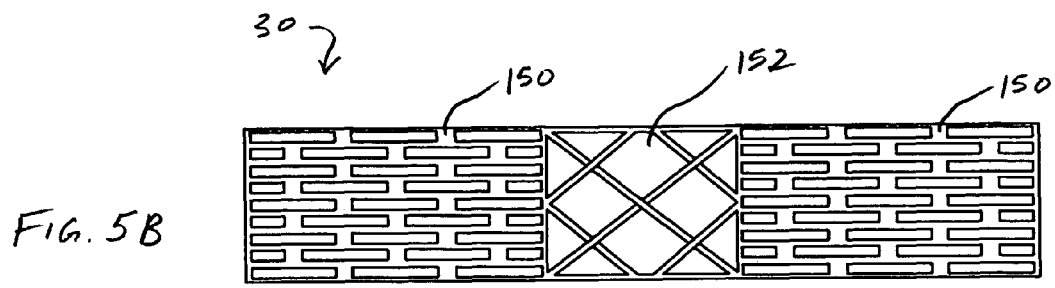
FIGS. 5B-5D are schematic side views of various stents, each having a central portion and adjacent end portions, according to various embodiments of the invention.
Figure 5C:
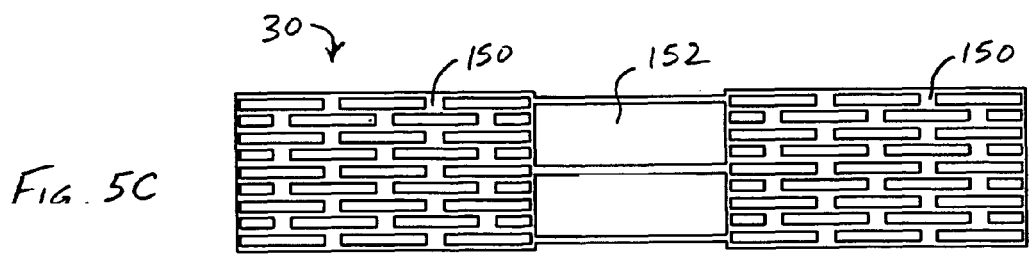
Figure 5D:
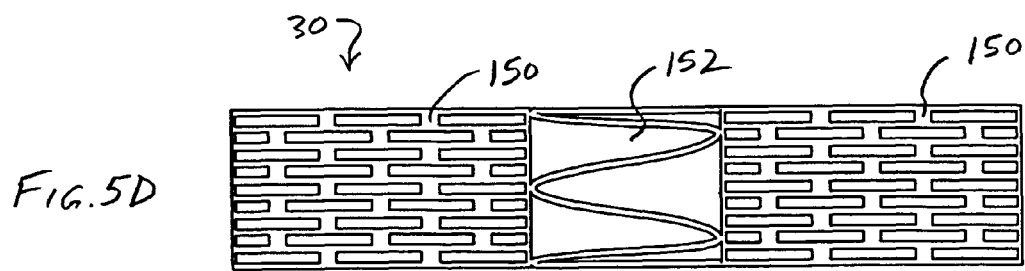

In other embodiments, end portions 150 have a higher density of struts or material per unit length than side access portion 152. In other words, end portions 150 may be constructed of more dense material, may have a more dense pattern of struts, or both, relative to side access portion 152 in some embodiments. As shown in FIG. 5B, in one embodiment end portions 150 may have straight or I-shaped slots, and side access portion 152 may have a woven or crosshatched geometry of diagonal struts. In another embodiment, as in FIG. 5C, side access portion 152 has linear struts aligned along the longitudinal axis of stent 30. In yet another embodiment, as in FIG. 5D, side access portion 152 has an undulating pattern. Various other embodiments of stents may have any other suitable configurations including a side access portion 152 with openings like those described above in reference to FIGS. 3A and 3B or 4A and 4B, but which are larger than adjacent end portions 150. In various embodiments, stents 30 may be deployed by a number of different techniques. For example, in some embodiments, end portions 150 are balloon expandable while side access portion 152 is self-expanding, for example a side access portion 152 comprising shape memory or superelastic material. In other embodiments, all of stent 30 (both end portions 150 and side access portion 152) may be either self-expanding or balloon expandable. In some embodiments, an expandable member may be advanced through an opening in side access portion 152 and expanded to increase the size of the opening. Some embodiments may further include coupling means such as hooks, tabs or annular rib or rim on either or both of the main branch stent and side branch stent for coupling a side branch stent with side access portion 152. Side access portion 152 may be disposed centrally along the stent or may be offset toward the distal or proximal ends of the stent, and may even be at either end of the stent, as appropriate for the lesion to be treated. Multiple side access portions may also be included in the same stent.

Figure 6A:
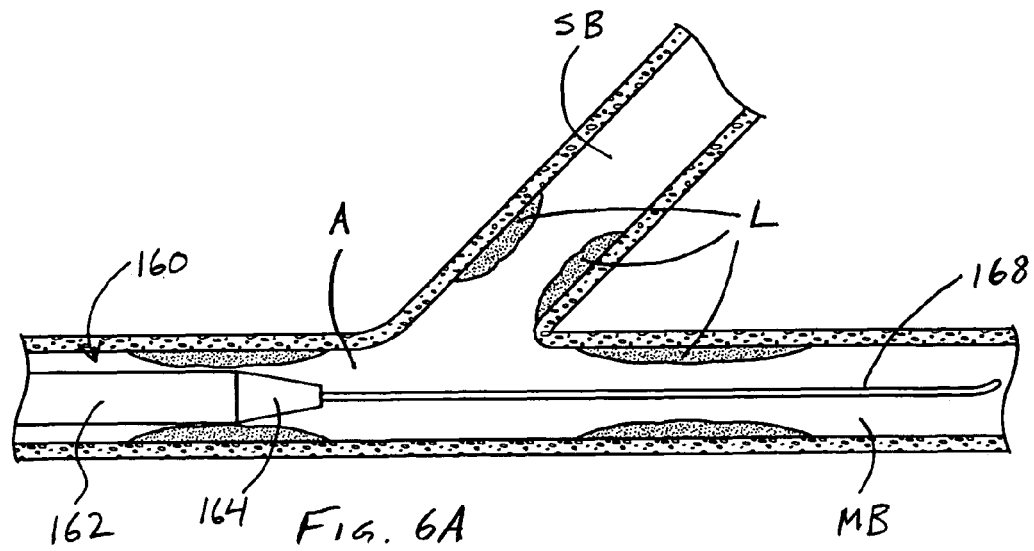
FIGS. 6A-6H are side cutaway views illustrating a method for treating lesions in a bifurcated vessel using a stent delivery catheter according to one embodiment of the invention.

Referring now to FIGS. 6A-6H, one embodiment of a method for treating lesions in a bifurcation using a stent delivery catheter of the invention will be described. While the invention will be described in the context of coronary artery treatment, the invention is useful in any of a variety of bifurcated blood vessels and other body lumens in which stents are deployed, including the carotid, femoral, iliac and other arteries, as well as veins and other fluid-carrying vessels. A guiding catheter (not shown) is first inserted into a peripheral artery such as the femoral and advanced to the ostium of the target coronary artery A. Referring to FIG. 6A, a guidewire 168 is then inserted through the guiding catheter into the coronary artery A where one or more lesions L are to be treated. The proximal end of guidewire 168 is then inserted through a nosecone 164 of a stent delivery catheter 160 outside the patient's body, and stent delivery catheter 160 is slidably advanced over guidewire 168 and through the guiding catheter into the coronary artery A. During advancement, a sheath 162 is extended to nosecone 164 to surround the expandable member.

Figure 6B:
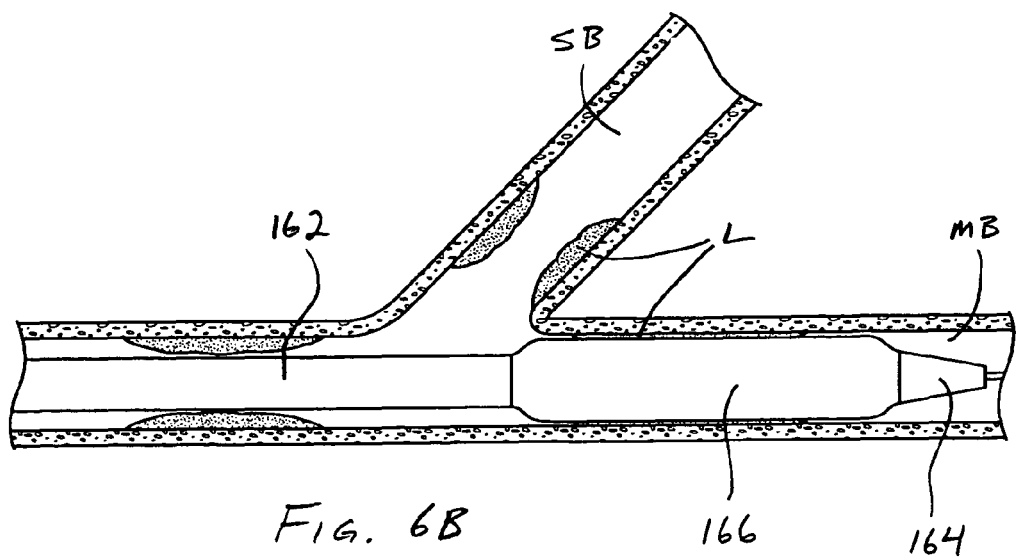

As shown in FIG. 6B, stent delivery catheter 160 is positioned through a lesion L to be treated such that nosecone 164 is distal to the lesion L. In one embodiment, catheter 160 is positioned first to treat a lesion in a main branch vessel MB of the coronary artery A. In alternative embodiments, catheter 160 may first be used to treat a lesion in a side branch vessel SB of the artery A.

Optionally, as shown in FIG. 6B, sheath 162 may be retracted and expandable member 166 expanded to predilate lesion L prior to stent deployment. Stent delivery catheter 160 may be used for predilitation by retracting sheath 162 along with stent segments (not shown) to expose an extremity of expandable member 166 long enough to extend through the entire lesion. (Alternatively, predilatation may be performed prior to introduction of stent delivery catheter 160 by inserting a separate angioplasty catheter over guidewire 168 and dilating lesion L.) This may be done while delivery catheter 160 is positioned proximally of lesion L or with expandable member 166 extending through lesion L. In some embodiments, fluoroscopy enables the user to visualize the extent of sheath retraction relative to lesion L by observing the position of a marker on sheath 162 relative to a marker at the distal end of expandable member 166. To allow stent segments to move proximally relative to expandable member 166, force is released from pusher tube 36 and valve member 50 (FIGS. 2A and 2B) engages and draws the stent segments proximally with sheath 162. With the appropriate length of expandable member 166 exposed, inflation fluid is introduced through inflation lumen 34 to inflate expandable member 166 distally of sheath 162 and thereby dilate lesion L. Expandable member 166 is then deflated and retracted within sheath 162 while maintaining force on the pusher tube so that stent segments are positioned up to the distal end of expandable member 166, surrounded by sheath 162. Alternative embodiments of devices and methods for lesion predilatation are described in detail in U.S. patent application Ser. No. 10/794,405, which was previously incorporated by reference.

Figure 6C:
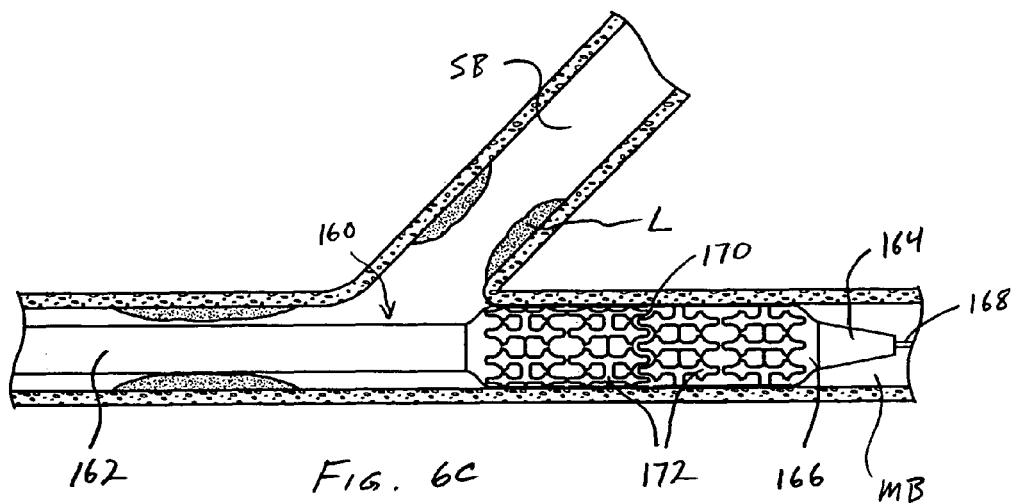

Referring now to FIG. 6C, following any predilatation, stent delivery catheter 160 is repositioned in the main branch so that nosecone 164 is distal to the lesion (main branch MB lesion not visible in FIG. 6C). Sheath 162 is then retracted to expose a stent 170 having an appropriate number of stent segments 172 to cover the lesion. As sheath 162 is drawn proximally, force is maintained against pusher tube 36 so that stent segments 172 remain positioned up to the distal end of expandable member 166. Expandable member 166 is then inflated by delivering inflation fluid through inflation lumen 34, and the exposed distal portion of expandable member 166 expands so as to expand stent segments 172 thereon into engagement with the lesion. If predilatation was not performed, lesion L may be dilated during the deployment of stent segments 172 by appropriate expansion of expandable member 166. Sheath 162 constrains the expansion of the proximal portion of expandable member 166 and stent segments within sheath 162.

Figure 6D:
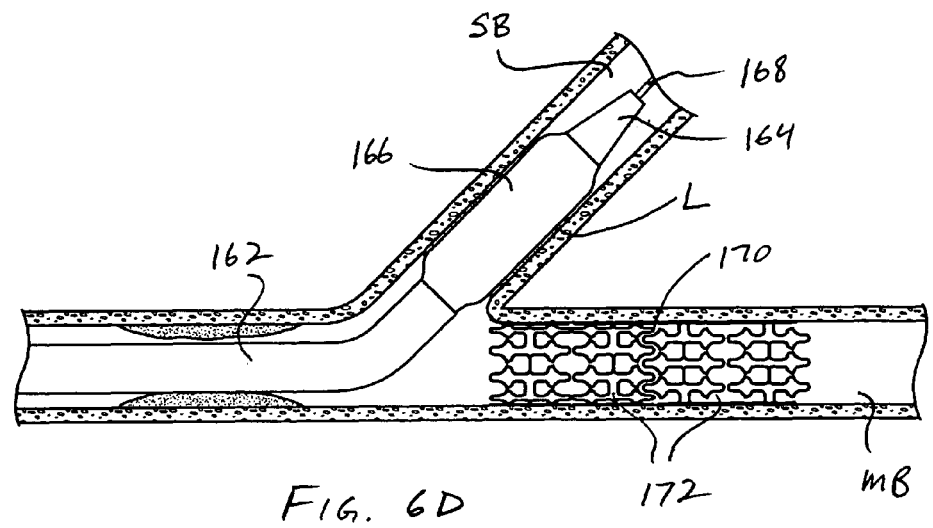

Expandable member 166 is then deflated, leaving stent segments 172 in a plastically-deformed, expanded configuration within lesion L, as shown in FIG. 6D. With stent segments 172 deployed, expandable member 166 may be retracted within sheath 162, again maintaining force against pusher tube 36 to position a second set of stent segments (not shown) at the distal end of expandable member 166. Expandable member 166 is moved proximally relative to the second stent segments until the distal-most stent segment engages stop 78 (FIGS. 2A-2B), thereby placing second stent segments in position for deployment. Stent delivery catheter 160 is then ready to be repositioned at a different lesion L in the side branch vessel SB, as shown in FIG. 6D, or in the main branch MB in other embodiments. Guidewire 168 is first advanced into side branch SB, and catheter 160 is advanced over guidewire 168. Sheath 162 is again retracted and expandable member 166 expanded to dilate lesion L. Advantageously, multiple lesions of various lengths may be treated in this way without removing stent delivery catheter 160 from the patient's body.

Figure 6E:
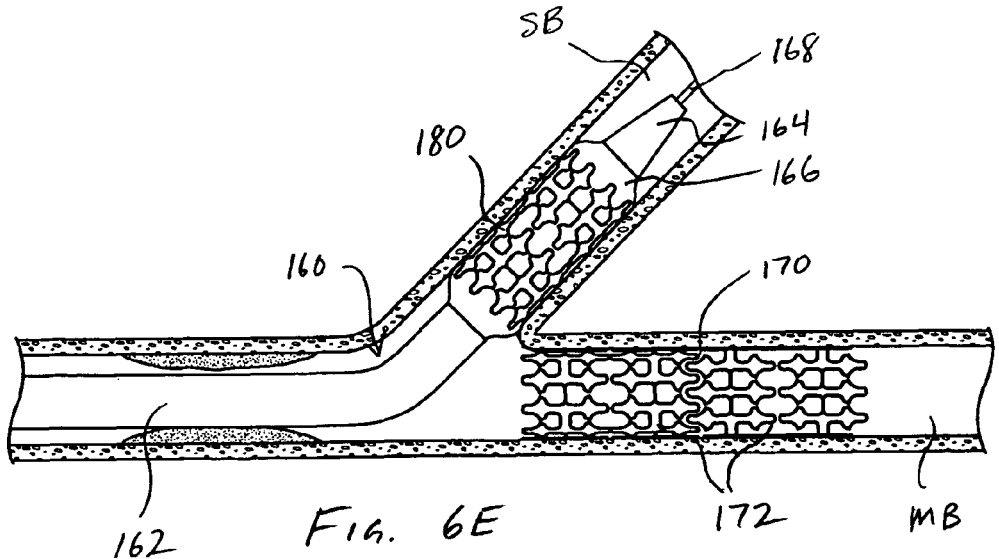
Figure 6F:
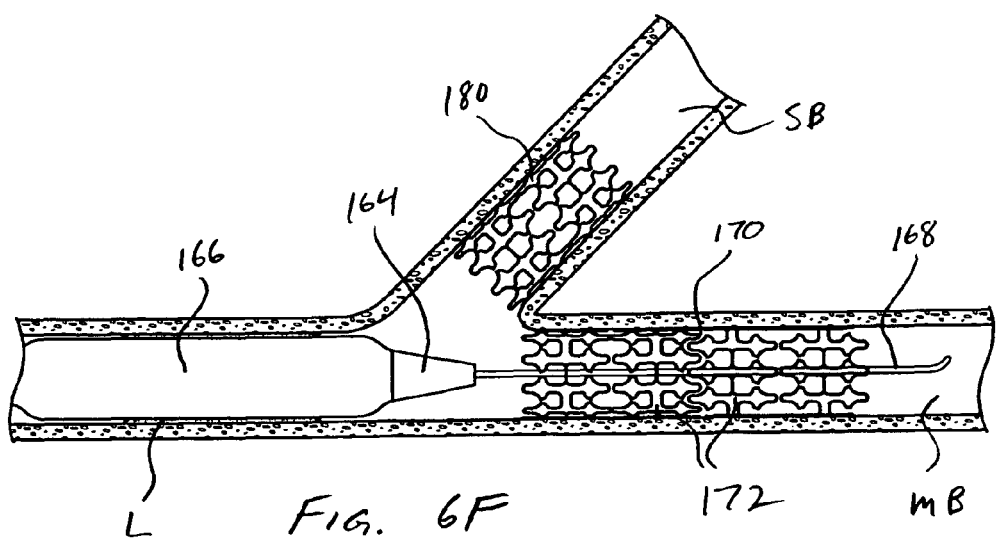
Figure 6G:
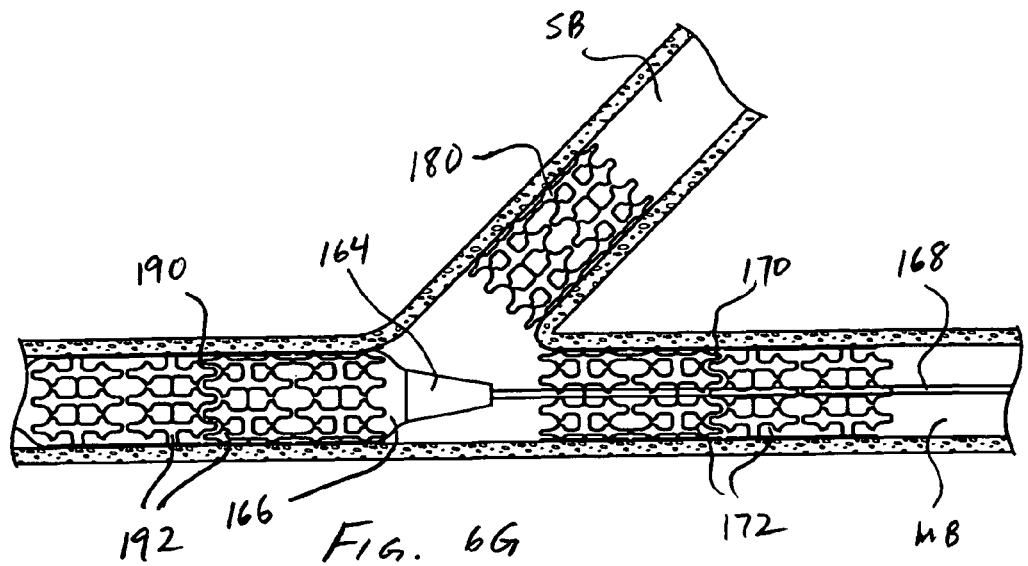
Figure 6H:
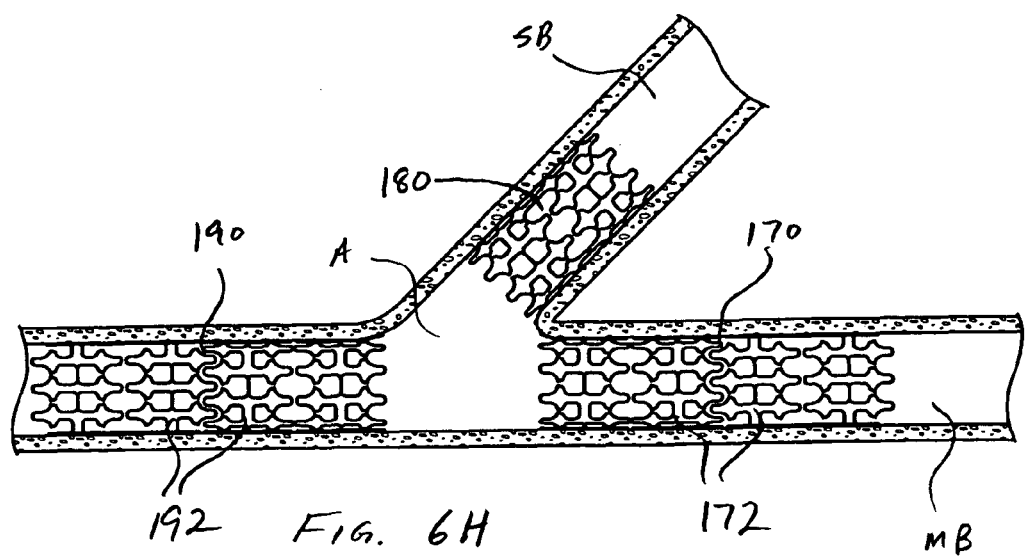

Referring now to FIG. 6E, once positioned in the side branch SB, stent delivery catheter 160 may be used to deploy a second stent 180 at the lesion L in the side branch SB. The method for stent deployment may be carried out as described above. Delivery catheter 160 may then be removed from the side branch SB, realigned in the main branch, and expandable member 166 again inflated to dilate a third lesion L, as shown in FIG. 6F. As shown in FIG. 6G, stent delivery catheter 160 may next be used to deploy a third stent 190 having one or more stent segments 190 at another lesion L in the main branch MB. FIG. 6H shows three stents 170, 180, 190 in place in the main branch MB and side branch SB of the artery A, after stent delivery catheter 160 has been removed. In various alternative techniques, only one stent may be placed in each of the main and side branches, the side branch stent may be placed before the main branch stent, multiple stents may be placed in the side branch vessel, and or the like. Any suitable combination of stent placements is contemplated according to various embodiments of the invention. Furthermore, when movement of the pusher tube, sheath, or stent segments is described in relation to other components of the delivery catheter of the invention, such movement is relative and will encompass: moving the sheath, pusher tube, or stent segments while keeping the other component(s) stationary; keeping the sheath, pusher tube or stent segments stationary while moving the other component(s); or moving multiple components simultaneously relative to each other.

Figure 7A:
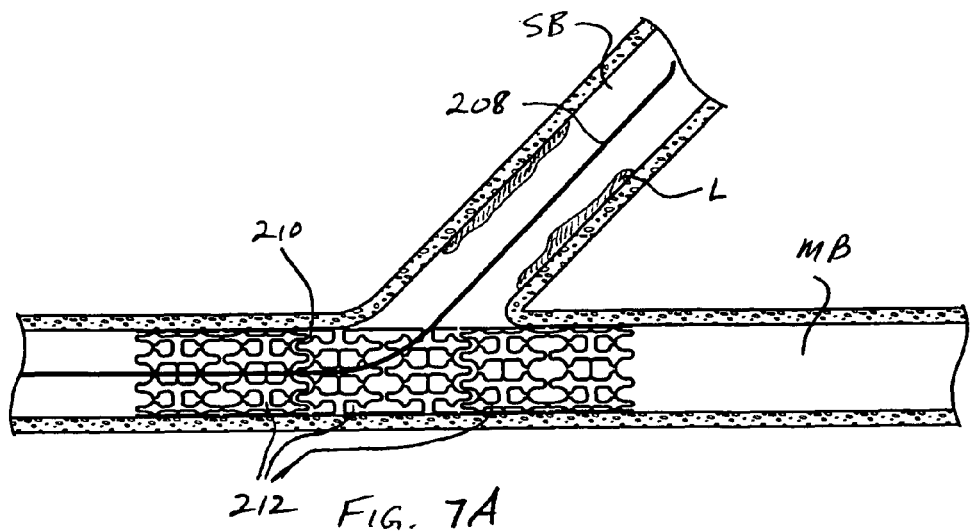
FIGS. 7A-7D are side cutaway views illustrating a method for treating lesions in a bifurcated vessel using a stent delivery catheter according to another embodiment of the invention.

Referring now to FIGS. 7A-7D, an alternative method for treating a bifurcated vessel is illustrated. As shown in FIG. 7A, a first stent 210 preferably having multiple stent segments 212 may be placed in the manner described above in a main branch MB of a vessel such that a central portion of first stent 210 crosses an ostium of (opening into) a side branch SB of the vessel. A guidewire 208 may then be extended through an opening in the sidewall of the central portion of first stent 210 into side branch SB and up to or past a side branch lesion L.

Figure 7B:
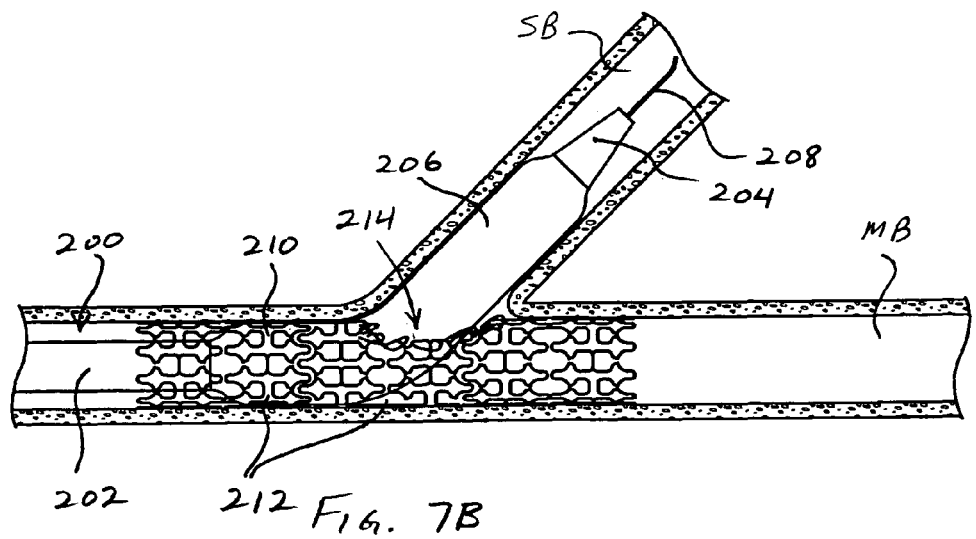

As shown in FIG. 7B, a stent delivery catheter 200 may then be advanced over guidewire 208, into side branch SB to a position for treating the lesion L. In some embodiments, a sheath 202 will first be retracted proximally from nosecone 204 to expose and allow expansion of an expandable member 206 to predilate the lesion L. In some embodiments, a portion of expanded expandable member 206 will extend through a sidewall opening 214 in first stent 210, and may be used to expand sidewall opening 214 either before or at the same time as it predilates the lesion L, deforming the struts around sidewall opening 214 to create a larger opening of a size sufficient to receive a second stent therethrough.

Figure 7C:
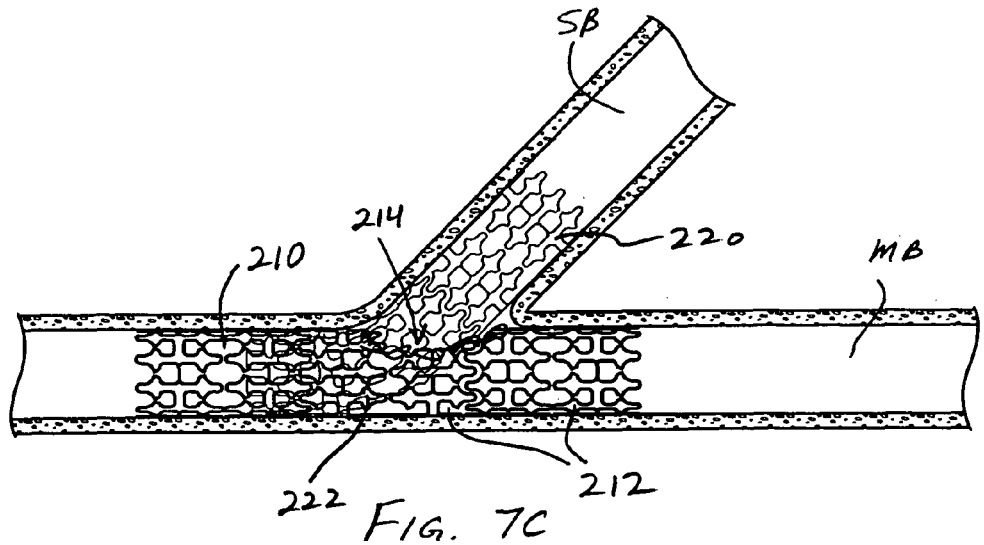

Referring now to FIG. 7C, a second stent 220 may then be placed in side branch SB using stent delivery catheter 200 (removed from FIG. 7C for clarity). In some embodiments, as in FIGS. 7C and 7D, second stent 220 may extend through side-wall opening 214 of first stent 210, to extend back into the main branch MB, thus having a bend or "elbow" to conform to the longitudinal axis of the main branch. In alternative embodiments, the second stent may extend up to but not through sidewall opening 214, may extend up to and attach to sidewall opening 214, may be spaced apart from sidewall opening 214, or the like.

Figure 7D:
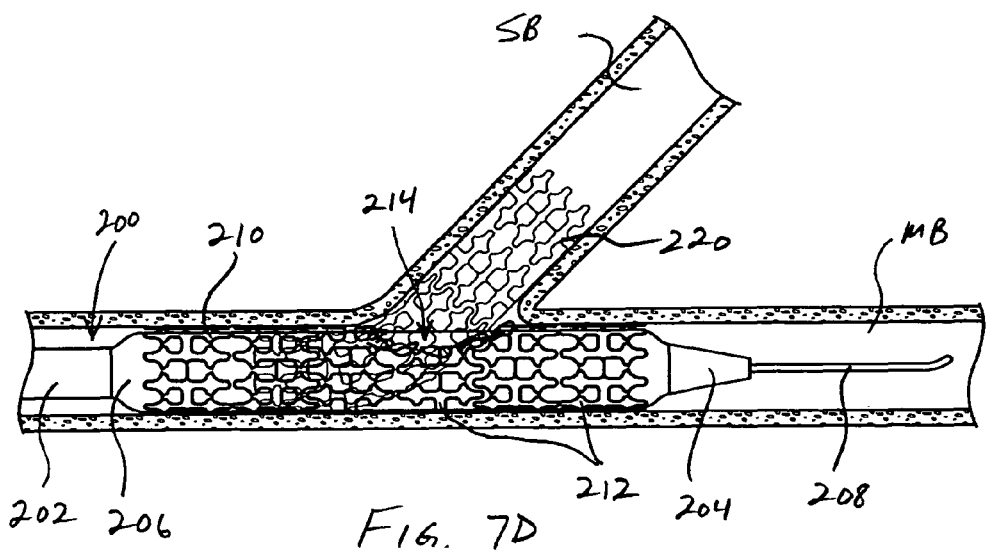
Figure 7E:
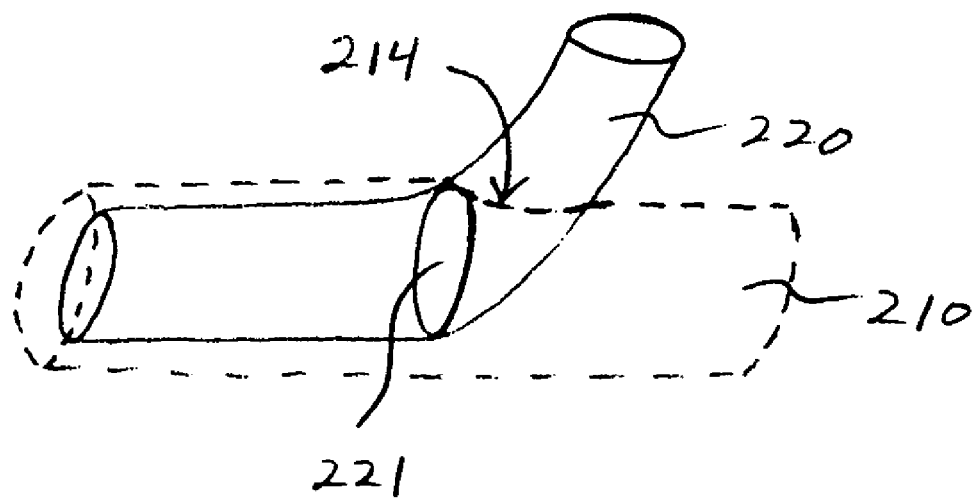
FIG. 7E is a schematic side view of two overlapping stents placed according to a method as in FIGS. 7A-7D.

As shown in FIGS. 7D and 7E, in one embodiment in which second stent 220 extends into the main branch MB, stent delivery catheter 200 may be advanced into main branch MB again, after placement of second stent 220, and expandable member 206 may be expanded so as to expand an opening 221 in the "elbow portion" of second stent 220 in alignment with the passage through first stent 210. FIG. 7E schematically shows first stent 210 overlapping second stent 214, the latter of which includes opening 221 in the "elbow portion" of the stent 214. Such expansion of an opening of second stent 220 helps to prevent disruption of blood flow through the main branch MB due to the presence of second stent 220 within the main branch MB.

Figure 8A:
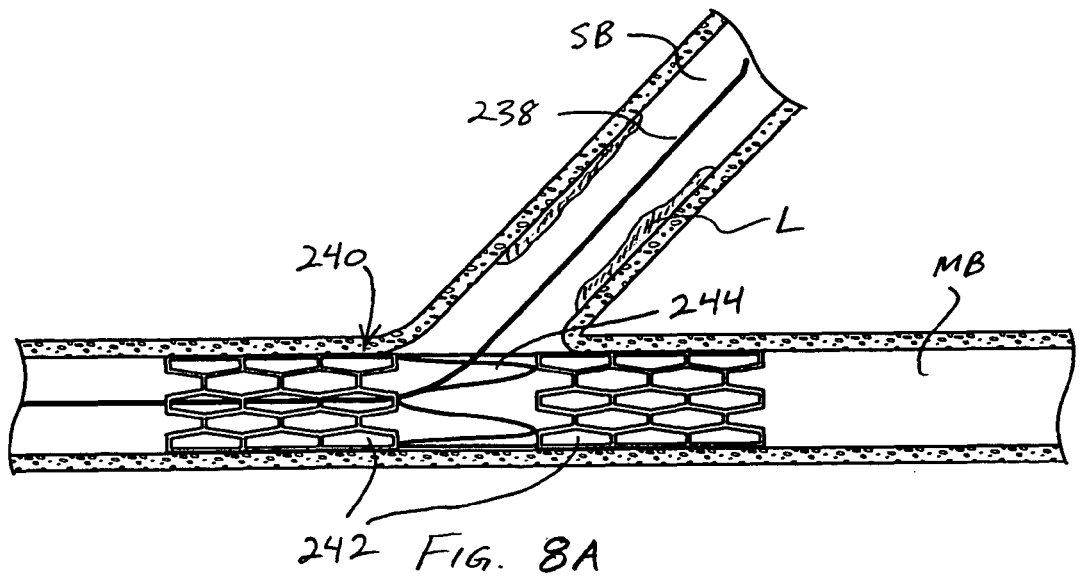

With reference now to FIGS. 8A-8D, another embodiment of a method for treating bifurcated vessels is described. As shown in FIG. 8A, a first stent 240 is delivered via a stent delivery catheter (shown in FIG. 8B) in a main branch MB of the vessel, such that a central portion 244 of first stent 240 is positioned at an ostium of a side branch SB. First stent 240 is generally configured as the stents described above with reference to FIGS. 5A-5D, thus having central portion 244 with one or more large sidewall openings and adjacent end portions 242 having smaller (or "higher density") sidewall openings. In one embodiment, central portion 244 is self-expanding while end portions 242 are balloon expandable. Central portion 244 may be positioned relative to the side branch SB ostium using fluoroscopy or any other suitable technique. A guidewire 238 may then be extended through a sidewall opening in central portion 244, into the side branch SB and up to or past a side branch lesion L.

Figure 8B:
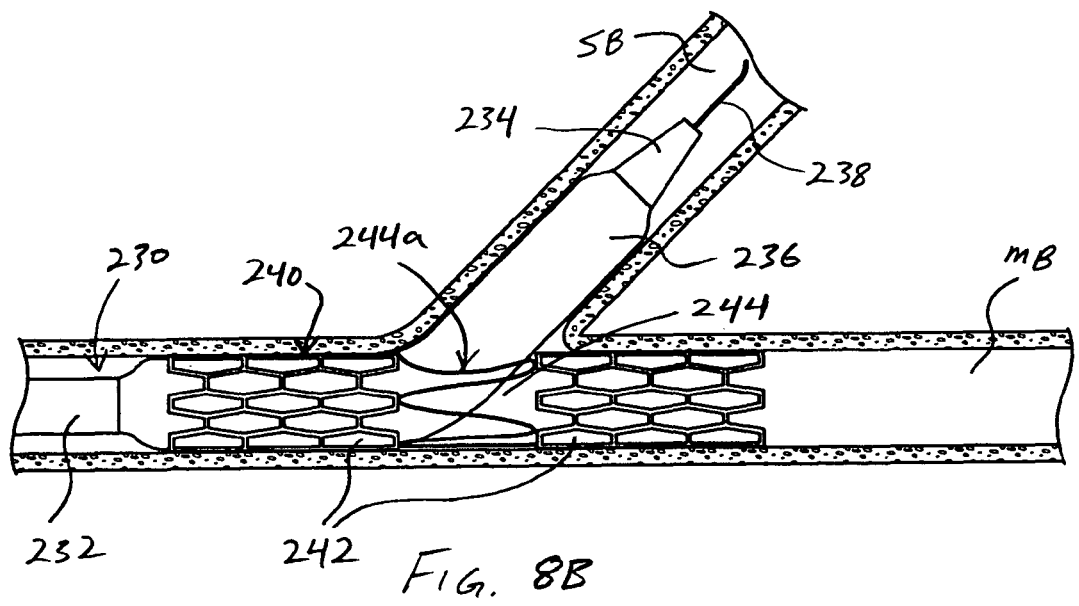

As illustrated in FIG. 8B, a stent delivery catheter 230 may then be passed through the sidewall opening, over guidewire 238, and into the side branch SB. A sheath 232 may be retracted from the nosecone 234 to expose and allow expansion of an expandable member 236, to both predilate the lesion L and to expand the sidewall opening in central portion 244 by deforming or deflecting one or more struts 244a of central portion 244 adjacent the sidewall opening. As shown in FIG. 8C, delivery catheter 230 may then be used to deploy a second stent 250, as described above. Second stent 250 may also include a central portion 254 having large sidewall openings and adjacent end portions 252 having smaller sidewall openings. Again, as shown in FIG. 8D, delivery catheter 230 may be repositioned in the main branch MB after delivery of first stent 240 to expand a sidewall opening in second stent 250 to enhance blood flow through the main branch MB. The expanded opening in second stent 250 may in some embodiments lie in the central portion 254 of second stent 250.

While the foregoing description of the invention is directed to a stent delivery catheter for deploying stents into vascular lumens to maintain patency, various other types of wire-guided catheters also may embody the principles of the invention. For example, catheters for deployment of prosthetic devices such as embolic coils, stent grafts, aneurism repair devices, annuloplasty rings, heart valves, anastomosis devices, staples or clips, as well as ultrasound and angiography catheters, electrophysiological mapping and ablation catheters, and other devices may also utilize the principles of the invention.

Although the above is complete description of the preferred embodiments of the invention, various alternatives, additions, modifications and improvements may be made without departing from the scope thereof, which is defined by the claims.

What is claimed is:

1. A method of treating one or more lesions in a vessel, the vessel having a main branch and a side branch branching from the main branch at a bifurcation, the main branch having a lesion with a length, the method comprising:
    providing a delivery catheter having an expandable member and a plurality of stent segments disposed on the delivery catheter and axially positionable over the expandable member, the plurality of stent segments comprising a first, a second, and a third stent segment, wherein each of the plurality of stent segments when unexpanded are in direct contact with but not fixedly attached to respective adjacent stent segments, each of the plurality of stent segments are capable of being individually and fully expanded, and each of the plurality of stent segments together with respective adjacent segments are capable of being simultaneously expanded;
    positioning the delivery catheter in the main branch;
    selecting a length of a first stent according to the length of the lesion to be treated in the main branch;
    adjusting the length of the first stent according to the selected length while the delivery catheter remains in the vessel, wherein adjusting the length comprises selecting a first group of adjacent segments from the plurality of stents segments, wherein the first group includes at least the first and second stent segments;
    axially separating the first stent from a second stent when unexpanded so that the first and second stent are separately deployable, the second stent comprising at least the third stent segment;
    radially expanding the expandable member thereby radially expanding the first stent, wherein expanding the first stent comprises concurrently expanding the first group in the main branch while the second stent remains undeployed on the delivery catheter;
    positioning the delivery catheter in the side branch; and
    radially expanding the expandable member thereby radially expanding the second stent in the side branch, and wherein the delivery catheter remains in the vessel between radially expanding the first and second stents.

2. A method as in claim 1 wherein the plurality of stents comprise a fourth stent segment, the method further comprising deploying the fourth stent segment from the delivery catheter in the main branch or the side branch without removing the delivery catheter from the vessel.

3. A method as in claim 1 wherein the first stent comprises a plurality of circumferentially and longitudinally arranged openings in a sidewall thereof, each opening of the plurality expandable to allow the deployment of a stent therethrough, the method further comprising:
    positioning the delivery catheter through one of the openings; and
    deploying a stent with the delivery catheter positioned through the one opening.

4. A method as in claim 3, wherein each of the plurality of openings are expandable to a diameter substantially equal to an expanded diameter of at least one of the first, second, or third stent segments when deployed in the vessel.

5. A method as in claim 1 wherein the second stent comprises a plurality of separable stent segments.

6. A method as in claim 5, wherein the selected length of the first stent is sufficient to allow the first stent to substantially traverse the lesion in the main branch; and further comprising:
    selecting a length of the second stent according to the length of a lesion in the side branch;
    adjusting the length of the second stent according to the selected length of the second stent while the delivery catheter remains in the vessel, wherein adjusting the length comprises selecting a second group of adjacent segments from the plurality of stents segments, wherein the second group includes at least the third stent segment and an adjacent stent segment,
    wherein the first stent and second stent comprise a different number of stent segments.

7. A method as in claim 6, wherein the step of adjusting the length of the first or second stent comprises moving a sheath disposed at least partially over the delivery catheter.

8. A method as in claim 6, wherein the step of adjusting the length of the first or second stent comprises moving a pusher tube disposed at least partially over the delivery catheter.

9. A method as in claim 1 wherein the first stent has a different overall length than the second stent.

10. A method as in claim 1 wherein the first stent is deployed before the second stent.

11. A method as in claim 1 wherein the second stent is deployed before the first stent.

12. A method as in claim 1 wherein the first and second stent each has a portion in the main branch.

13. A method as in claim 1 further comprising
    adjusting the length of the second stent before deploying the second stent while the delivery catheter remains in the vessel, wherein adjusting the length comprises selecting a second group of adjacent segments from the plurality of stents segments, wherein the second group includes at least the third stent segment and an adjacent stent segment.

14. A method as in claim 1 further comprising
    dilating at least one lesion in the vessel using the expandable member on the delivery catheter without a stent disposed thereon before deploying at least one of the first and second stents.

15. A method of treating one or more lesions in a vessel, the vessel having a first branch and a second branch meeting at a bifurcation, the first branch having a lesion with a length, the method comprising:

providing a delivery catheter having an expandable member and a plurality of stents disposed on the delivery catheter and axially positionable over the expandable member, the plurality of stent segments comprising a first, a second, and a third stent segment, each of the plurality of stent segments when unexpanded are in direct contact with but not fixedly attached to respective adjacent stent segments, wherein each of the plurality of stent segments are capable of being individually expanded, and each of the plurality of stent segments together with respective adjacent segments are capable of being simultaneously expanded;

positioning the delivery catheter in the first branch;

selecting a length of a first stent according to the length of the lesion to be treated in the first branch;

adjusting the length of the first stent according to the selected length while the delivery catheter remains in the vessel, wherein adjusting the length comprises selecting a first group of adjacent segments from the plurality of stents segments, wherein the first group includes at least the first and second stent segments;

axially separating the first stent from a second stent when unexpanded so that the first and second stent are separately deployable, the second stent comprising at least the third stent segment;

radially expanding the expandable member thereby radially expanding the first stent, wherein expanding the first stent comprises concurrently expanding the first group in the first branch, a portion of the first group being disposed across the bifurcation while the second stent remains undeployed on the delivery catheter;

positioning the delivery catheter in the second branch through an opening in a sidewall of the first stent; and radially expanding the expandable member thereby radially expanding the second stent, and wherein at least a portion of the third stent segment is disposed in the second branch, wherein the delivery catheter remains in the vessel between radially expanding the first and second stents.

16. The method of claim 15 further comprising dilating the opening in the sidewall of the first stent by expanding the expandable member on the delivery catheter.

17. The method of claim 16 wherein before dilating, the opening in the sidewall of the first stent is I-shaped.

18. The method of claim 15 wherein the first stent has a first portion with a plurality of first sidewall slots and a second portion with a plurality of second sidewall slots, the first slots being larger than the second slots.

19. The method of claim 18 wherein the opening in the sidewall of the first stent comprises one of the first slots, and wherein the first stent is deployed so that at least one of the first slots is aligned with the bifurcation.

20. The method of claim 15 wherein the first stent has a different geometry than the second stent.

21. The method of claim 15 wherein the first stent has a different length than the second stent.

22. The method of claim 15 wherein the second stent comprises a plurality of separable stent segments.

23. A method as in claim 22, wherein the selected length of the first stent is sufficient to allow the first stent to substantially traverse the lesion in the first branch, and the method further comprises:

selecting a length of the second stent according to the length of a lesion in the second branch;

adjusting the length of the second stent according to the selected length of the second stent while the delivery catheter remains in the vessel, wherein adjusting the length comprises selecting a second group of adjacent segments from the plurality of stents segments, wherein the second group includes at least the third stent segment and an adjacent stent segment, wherein the first stent and second stent comprise a different number of stent segments.

24. A method as in claim 23, wherein the step of adjusting the length of the first or second stent comprises moving a sheath disposed at least partially over the delivery catheter.

25. A method as in claim 23, wherein the step of adjusting the length of the first or second stent comprises moving a pusher tube disposed at least partially over the delivery catheter.

26. The method of claim 15 wherein the first stent comprises a plurality of circumferentially and longitudinally arranged sidewall openings, each opening of the plurality expandable to allow the deployment of a stent therethrough and at least one opening of the plurality of openings is aligned with the first branch of the vessel, the method further comprising expanding the at least one expandable opening using the expandable member on the delivery catheter without a stent disposed thereon.

27. A method as in claim 26, wherein each of the plurality of openings are expandable to a diameter substantially equal to an expanded diameter of at least one of the first, second, or third stent segments when deployed in the vessel.

* * * * *